United States Patent
Gopalakrishnan

(10) Patent No.: US 12,211,616 B2
(45) Date of Patent: Jan. 28, 2025

(54) MULTIFUNCTIONAL TELEMETRY APPARATUS FOR REAL-TIME EMERGENCY SUPPORT

(71) Applicant: Muralidharan Gopalakrishnan, Thane (IN)

(72) Inventor: Muralidharan Gopalakrishnan, Thane (IN)

(73) Assignee: Muralidharan Gopalakrishnan, Maharashtra (IN)

( * ) Notice: Subject to any disclaimer, the term of this patent is extended or adjusted under 35 U.S.C. 154(b) by 280 days.

(21) Appl. No.: 17/966,785

(22) Filed: Oct. 15, 2022

(65) Prior Publication Data

US 2023/0078549 A1    Mar. 16, 2023

Related U.S. Application Data

(63) Continuation-in-part of application No. 16/645,811, filed as application No. PCT/IB2018/058718 on Nov.
(Continued)

(51) Int. Cl.
*G16H 40/63* (2018.01)
*A61B 5/00* (2006.01)
(Continued)

(52) U.S. Cl.
CPC .......... *G16H 40/63* (2018.01); *A61B 5/0002* (2013.01); *A61B 5/0077* (2013.01);
(Continued)

(58) Field of Classification Search
CPC ...... G16H 40/63; G16H 40/67; A61B 5/0002; A61B 5/0077; A61B 5/0205; A61B 5/721;
(Continued)

(56) References Cited

U.S. PATENT DOCUMENTS

| 5,512,879 A * | 4/1996 | Stokes | G08B 21/0288 455/100 |
| 2014/0118140 A1* | 5/2014 | Amis | G08B 25/08 340/539.13 |

(Continued)

*Primary Examiner* — Quan Zhen Wang
*Assistant Examiner* — Rajsheed O Black-Childress

(57) ABSTRACT

Multifunctional telemetry apparatus for real-time emergency support comprising biosensors set of electrical biosensors set, green LEDs, red LEDs, infrared LEDs, near infrared LEDs and photodetector set and temperature biosensor, accelerometer, pressure sensor set and wireless antenna, which enables the life-support network to infer and monitor user's present condition through a plurality of real-time biological information, clinical emergency conditions, movement data and events of victimizer unstrapping the apparatus. The embodiments of the multifunctional telemetry apparatus to track emergency situations through analysis of tracking information even in moving conditions or victimizer based emergency situation without active inputs or active involvement from user. Classified clinical emergency and child tracking applications synchronized to the emergency support apparatus, and these applications operated by the life-support having classified trigger commands and tracking information displayed in a manner to help efficiently mitigate emergency risks. The apparatus configured through novel communication means to communicate to life-support network even with no access to standard communication channels.

17 Claims, 27 Drawing Sheets

Related U.S. Application Data 6, 2018, now Pat. No. 1,176,365, application No. 17/966,785 is a continuation-in-part of application No. 16/645,816, filed as application No. PCT/IB2018/058760 on Nov. 8, 2018, now abandoned, which is a continuation-in-part of application No. 16/127,228, filed on Sep. 11, 2018, now abandoned, and a continuation-in-part of application No. 16/127,236, filed on Sep. 11, 2018, now abandoned.

(60) Provisional application No. 62/638,315, filed on Mar. 5, 2018, provisional application No. 62/557,069, filed on Sep. 11, 2017.

(51) Int. Cl.
| | | |
|---|---|---|
| *A61B 5/0205* | (2006.01) | |
| *G08B 21/02* | (2006.01) | |
| *H04L 45/12* | (2022.01) | |
| *H04W 84/18* | (2009.01) | |

(52) U.S. Cl.
CPC ............ *A61B 5/0205* (2013.01); *A61B 5/721* (2013.01); *G08B 21/0202* (2013.01); *H04L 45/12* (2013.01); *A61B 2505/01* (2013.01); *A61B 2560/0214* (2013.01); *A61B 2560/0443* (2013.01); *A61B 2562/0204* (2013.01); *A61B 2562/0219* (2013.01); *A61B 2562/0247* (2013.01); *H04W 84/18* (2013.01)

(58) Field of Classification Search
CPC ........ A61B 2505/01; A61B 2560/0214; A61B 2560/0443; A61B 2562/0204; A61B 2562/0219; A61B 2562/0247; A61B 5/4806; A61B 5/6802; A61B 5/021; A61B 5/024; A61B 5/02405; A61B 5/0816; A61B 5/14532; A61B 5/14542; A61B 5/165; A61B 5/4812; A61B 5/4818; A61B 5/6831; A61B 5/7225; A61B 5/0022; A61B 5/02055; A61B 5/1112; G08B 21/0202; G08B 21/0288; G08B 25/016; H04L 45/12; H04W 84/18

See application file for complete search history.

(56) References Cited

U.S. PATENT DOCUMENTS

| | | | |
|---|---|---|---|
| 2014/0329214 A1* | 11/2014 | Bitoun | G16H 20/70 434/262 |
| 2016/0262702 A1* | 9/2016 | Cho | A61B 5/318 |
| 2016/0287166 A1* | 10/2016 | Tran | A61B 5/74 |
| 2017/0109992 A1* | 4/2017 | Lin | G08B 21/0446 |
| 2018/0025605 A1* | 1/2018 | Thomas | H04W 4/029 455/90.1 |
| 2018/0228234 A1* | 8/2018 | Hathi | A41F 9/002 |
| 2020/0146550 A1* | 5/2020 | Tunnell | H04L 65/4015 |
| 2021/0169417 A1* | 6/2021 | Burton | A61B 5/4857 |
| 2022/0061767 A1* | 3/2022 | Goldstein | A61B 5/11 |
| 2023/0098445 A1* | 3/2023 | Leonhardt | G08B 21/0269 340/573.1 |

* cited by examiner

MULTIFUNCTIONAL TELEMETRY APPARATUS FOR REAL-TIME EMERGENCY SUPPORT

CROSS-REFERENCE TO RELATED APPLICATIONS

The present application claims priority as a continuation-in-part to pending U.S. patent application Ser. No. 16/645,811 entitled, "NON-INVASIVE MULTIFUNCTIONAL TELEMETRY APPARATUS AND REAL-TIME SYSTEM FOR MONITORING CLINICAL SIGNALS AND HEALTH PARAMETERS" filed on Mar. 10, 2020 (i.e. 03-10-2020), which was a national stage application of International Application No. PCT/IB2018/058718 filed on Nov. 6, 2018 (i.e. 11-06-2018) that claims priority to U.S. application Ser. No. 16/127,228 entitled "NON-INVASIVE MULTIFUNCTIONAL TELEMETRY APPARATUS AND SYSTEM FOR REAL-TIME MONITORING OF VITAL CLINICAL SIGNALS AND HEALTH PARAMETERS" filed on Sep. 11, 2018 (i.e. 09-11-2018) that claimed benefit of priority of U.S. provisional Application No. 62/557,069 filed on Sep. 11, 2017 (i.e. 09-11-2017), U.S. Provisional Application No. 62/638,315 entitled "Automated Bio-Telemetry apparatus for monitoring pulse rate, breathing rate, neural health, other clinical parameter and health data" filed on May 3, 2018 (i.e. 03-05-2018) and U.S. provisional Application No. 62/557,069 entitled "Method and Apparatus for live and telemetry clinical monitoring, life support and general wellness management" filed on Sep. 11, 2017 (i.e. 09-11-2017).

The present application claims priority as a continuation-in-part to pending U.S. patent application No. 16/645,816 entitled "AUTOMATED WIRELESS APPARATUS FOR REAL-TIME EMERGENCY SUPPORT" filed on Mar. 10, 2020 (i.e. 03-10-2020), which was a national stage application of International Application No. PCT/IB2018/058760 filed on Nov. 8, 2018 (i.e. 11-08-2018) that claims priority to U.S. application Ser. No. 16/127,236 entitled "AUTOMATED WIRELESS APPARATUS FOR REAL-TIME EMERGENCY SUPPORT" filed on Sep. 11, 2018 (i.e. 09-11-2018) that claimed benefit of priority of U.S. provisional Application No. 62/557,069 filed on Sep. 11, 2017 (i.e. 09-11-2017), U.S. Provisional Application No. 62/638,315 entitled "Automated Bio-Telemetry apparatus for monitoring pulse rate, breathing rate, neural health, other clinical parameter and health data" filed on May 3, 2018 (i.e. 03-05-2018) and U.S. provisional Application No. 62/557,069 entitled "Method and Apparatus for live and telemetry clinical monitoring, life support and general wellness management" filed on Sep. 11, 2017 (i.e. 09-11-2017).

TECHNICAL FIELD

The present invention relates to a multifunctional telemetry apparatus that efficiently mitigates the emergency situations without requiring an active involvement of user even in a victimizer involved situation.

BACKGROUND OF THE INVENTION

The current devices and technological innovations for emergency support applications utilize user inputs and location information to track and help a user in an emergency. Though the current innovations for emergency support can alleviate an emergency on real-time basis by providing relevant location data, but they require active user inputs for further inferring the emergency that effectively leaves an emergency condition unresolved. The user involvement in emergency situations must be minimized or otherwise eliminated to efficiently tackle emergency situations as a user may not be able to intervene themselves in such a situation. The active involvement of user in emergency situation may also pose further threat to a user, such as in an erratic attack by a victimizer on an innocent victim where victimizer may try to conceal the event by injuring or harming the innocent victim on noticing victim's activity towards emergency support (such as contacting a SOS or guardian network or proving user inputs).

The prior inventions for emergency support also do not support tracking important real-time information, other than location information or user inputs, for inferring current user condition. An emergency response network or life-support network can only take relevant moves and provide suitable mitigation support or responses on understanding the current user condition. Therefore, it is also essential to convey important tracking information in real-time basis that can help the life-support network and the emergency response network differentiate the emergency situation to effectively aid a user struck in an emergency (and also in situations where user cannot be actively involved).

The life-support network must be equipped with real-time tracking information along with classified emergency or alerting commands to escalate and avail for only the required mitigation support or response to effectively help a user in emergency situation. There may be an uncivilized attack by a victimizer on a helpless individual and in such a situation the life-support network of user cannot communicate real-time tracking information to anyone as it poses threat to privacy of helpless individual and can also otherwise aggravate the threat to the innocent individual. There may be situations in which a medico can only alleviate emergency and in a such situation it is important to not involve non-medicos. The prior art fails to disclose classified alert or emergency commands along with tracking information that are critically valuable to efficiently resolve the emergency.

Also, that the prior inventions do not provide solution for emergency support in situations where location information cannot be obtained or wireless communication cannot be established for tracking activity and current condition of user. The prior inventions for emergency support applications also fails to track victimizer actions in real-time without user actively revealing their involvement towards emergency support.

Therefore, there is need for a robust multifunctional telemetry apparatus for real-time emergency support that accounts all such factors and works in numerous problematic situations.

SUMMARY OF THE INVENTION

The aforementioned problems and deficiencies associated with the prior emergency support inventions are eliminated or reduced by the disclosed multifunctional telemetry apparatus for real-time emergency support. The disclosed multifunctional telemetry apparatus for real-time emergency support comprises a biosensing hardware with biosensors set and other sensors that tracks plurality of real-time biological information and other important real-time tracking information to infer current user condition. The plurality of real-time tracking information are displayed on a life-support application synchronized to the disclosed emergency support apparatus. The life-support network operating these life-support applications can use this real-time tracking information to provide suitable mitigation efforts or responses for emergency support. Also, these life-support applications have classified alert and emergency commands suitable for escalating the issue to only avail the required mitigation support or response for emergency that in turn improves the overall efficiency of the emergency support.

The hardware of the disclosed multifunctional telemetry apparatus for real-time emergency support is configured to track plurality of real-time biological information and clinical emergency conditions comprising heart rate, pulse rate variability, oxygen saturation, neural activity, breathing pattern, blood pressure levels, blood sugar levels, body temperature, sleep cycles, sleep apnea condition, hypoglycemia state, hyperglycemia state, congestive heart failure condition, CO poisoning condition, hypoxia condition, hypothermia condition, hyperthermia condition, stress condition, anxiety condition and seizure condition. This real-time biological information can be assessed by the life-support network or emergency response network to take suitable action and provide suitable response or mitigation efforts to save or protect the user in an emergency. The life-support application used by the life-support network displays the plurality of real-time biological information and clinical emergency conditions in such a manner that a medico can take quicker decisions to save a user in emergency, and also the life-support application displays the tracking information in such a manner that a non-medico of the life-support network can efficiently communicate the current condition of the user to the medico. Disclosed in this disclosure are flowcharts that are executed by the disclosed emergency support apparatus to extract these plurality of real-time biological information and clinical emergency conditions.

The disclosed multifunctional telemetry apparatus for real-time emergency support also considers a situation where a user is in an emergency when the user is moving. The hardware of the disclosed multifunctional telemetry apparatus for real-time emergency support is configured to eliminate such movement errors in tracking information. The disclosed emergency support apparatus also does not require active location or communication signals to track user movement activity and the disclosed emergency support apparatus has a 9-axis accelerometer to track plurality of movement data and the user condition. Disclosed in this disclosure are flowcharts that are executed by the disclosed emergency support apparatus to extract these plurality of movement data.

The multifunctional telemetry apparatus for real-time emergency support also accounts an emergency situation where victimizer may impede the user from availing emergency support. The hardware of disclosed emergency support apparatus comprises pressure sensor set placed in certain spots befitted to identify an event when victimizer unbuckles the emergency support apparatus. The pressure sensors placed in definite spots of the disclosed emergency support apparatus inclines the victimizer and enables the victimizer as a medium to trigger the emergency support for user, where a user input or involvement is not required to identify the emergency event.

The multifunctional telemetry apparatus for real-time emergency support includes power supply hardware components suited to alleviate a situation when an emergency support apparatus runs of power due to typical battery source draining, operating cycles and environmental conditions. The disclosed emergency support apparatus also mulls over possibility where a user in emergency may not have access to standard internet, mobile or satellite communication. The disclosed emergency support apparatus is configured to communicate through a SWARM network without access to standard communication channels.

The object of the invention is a robust multifunctional telemetry apparatus for real-time emergency support that works efficiently in numerous emergency situations and problematic circumstances while providing important tracking information in a manner that can help the life-support network classify the required emergency support and thus enabling quicker, safer and effective resolution to the emergency situation.

First Aspect

The hardware of the emergency support apparatus (i.e. multifunctional telemetry apparatus for real-time emergency support) is described in the first aspect. The emergency support apparatus comprises micro-controller with in-built memory, wireless antennae set of WLAN, Bluetooth, GSM and GPS, biosensor frontend, biosensors set, 9-axis accelerometer, pressure sensor set, touch display, mic, camera, power management unit, battery-supercapacitor set and energy harvester-supercapacitor set. The emergency support apparatus through the biosensor set of temperature sensor, blood glucose sensor, blood pressure sensor, pulse sensor and stress sensor is configured to extract plurality of real-time biological information and clinical emergency conditions including heart rate, pulse rate variability, oxygen saturation, neural activity, breathing pattern, blood pressure levels, blood sugar levels, body temperature, sleep cycles, sleep apnea condition, hypoglycemia state, hyperglycemia state, congestive heart failure condition, CO poisoning condition, hypoxia condition, hypothermia condition, hyperthermia condition, stress condition, anxiety condition and seizure condition.

In one specific preferred low-powered biosensing hardware architecture of the multifunctional telemetry apparatus for real-time emergency support, the biosensors set of temperature sensor, blood glucose sensor, blood pressure sensor, pulse sensor and stress sensor are at least one or more of optical sensors set of green LED, red LED, infrared LED, near infrared LED and photodetector set, a set of four electrical sensors and a non-contact temperature sensor. The inputs to the set of green LED, red LED, infrared LED, near infrared LED are reduced through an attenuation circuit integrated at LED frontend and the optical amplifier improves amplification of optical bio-signal response at the photodetector set. The multi-spectral signals from green LED, red LED, infrared LED and near infrared LED are generated based on the control commands through a gain programmable LED Frontend and a switch set. The switch set enables operation of multiple LEDs through a single LED frontend, which further makes the hardware compact and low-powered. The low-powered optical response signals recorded at the photodetector set is processed through a series of circuits for amplification, signal stabilization and noise filtering. An impedance analyzer IC of the hardware injects a low-powered AC signal through an attenuation circuit connected to electrical sensor E1 of the electrical sensors set (E1-E2-E3-E4) and the low powered AC signals are drained through the electrical sensor E4 of the electrical sensors set (E1-E2-E3-E4). Real and imaginary impedances of AC response signals are extracted through the impedance analyzer IC connected to a series of response processing circuits attached to the two electrical sensors E2-E3 of the electrical sensors set that are placed between the other two electrical sensors E1-E4 of the electrical sensors sets. The hardware of the emergency support apparatus includes a 9-axis accelerometer, whose axis is aligned with the biosensors set. The real-time bio-signals of AC signal response and optical response recorded by the internal microprocessor and are correlated with real-time accelerometer signals to remove movement errors in the bio-signals. The accelerometer is also analyzed to record a plurality of movement data.

The hardware of the multifunctional telemetry apparatus for real-time emergency support is configured to analyze the real-time bio-signals to compute the plurality of biological information. Peaks detected from the movement error free bio-signals are analyzed to compute average. heart rate, instantaneous heart rate and pulse rate variability. The recorded respective heart rate time intervals are plotted to extract HR tachogram. The pulse rate variability dataset are anlayzed for computing the autonomous neural activity coefficients of σ1, σ2, σ3, σ3/σ1, σ3/σ2, σ2/σ1. The bio-signals are analyzed through digital filters in bandwidths of HF, LF VLF, ULF and Meyer Band, and the power spectrum of the bio-signals are computed in these respective bands to extract autonomous neural activity assessment parameters of P1, P2, P3, P4 and P5. The movement error free bio-signals are analyzed for extrema to decouple the bio-signals into different waves and an iterative decoupling with frequency check is applied to obtain the low frequency breathing signals and meyer wave signals. The breathing signals are analyzed for peaks to compute continuous respiratory rate and average respiratory rate.

The extremum of the optical response and the user's input of real-time blood pressure values with respect to time are recorded. A ratio between optical intensity ratio of extremum of maxima and minima and that of user input of real-time computed are analyzed to compute the continuous blood pressure levels and diastolic pressure levels. The dual sensor configuration is utilized to estimate momentum loss in the blood vessel during the change of the peaking of the blood pressure cycle to compute mean pressure and the systolic pressure levels. Whereas, heart to device reference length is used in the cuff based apparatus to measure the mean arterial pressure (as an alternative to manual user inputs). The green LED, red LED and infrared LED response signals are correlated to the near infrared LED response signals to eliminate the blood flow fluctuations, tissue absorption, coherent errors and beat to beat fluctuations in the near infrared LED response signals. Then processed real-time near infrared are fitted over various current user input of blood sugar values in real-time to calibrate the biosensors and to compute the real-time blood sugar levels. The computed real-time blood sugar levels are analyzed for threshold values to detect hyperglycemia and hypoglycemia conditions.

The accelerometer values are analyzed to verify the user is in sleep or dormant state. The real-time signals of blood sugar levels, oxygen saturation, blood pressure levels, respiratory patterns, heart rate and temperature are compared to wake, sleep and activity data to verify the state of sleep and rest. After verification of the real time signals of avg. breathing rate, avg. systolic blood pressure and instantaneous heart rate signals are analyzed to track and compute the time periods of non-rapid eye movement sleep cycles and rapid eye movement sleep cycles. The instantaneous heart rate dataset are analyzed in a time interval of 30-60 seconds and for 5-7 BPM difference between the extremum of the dataset for falling and raising edges within a window of 9.5 seconds, and further in a time interval of 20-120 seconds to recognize sleep apnea condition. The respiratory pattern within the recognized sleep apnea condition is further verified for low and irregular pattern to further validate the sleep apnea condition. On recognizing the sleep apnea conditions, the time intervals of the sleep apnea are stored. On recognizing mild to severe conditions of sleep apnea, a warning message is sent to the user and the life-support network.

The recorded real-time biological information, accelerometer values and user calibration values are analyzed by the emergency support apparatus to recognize plurality of movement data, health conditions and clinical emergency conditions. On detecting realistic values of bio-signal data, the emergency support apparatus is started or sent to wake mode. Initially user inputs on the clinical data, health data and learning parameters are recorded for calibration. The real-time biological information of heart rate pattern, respiratory pattern, blood pressure levels pattern, blood sugar levels pattern, temperature, autonomous neural activity coefficients and parameters i.e. the vital signal data and the 9-axis accelerometer signals are analyzed to calibrate or detect the movement data of sleeping, sitting, standing, moving, running, sprinting and resistance training. The heart rate pattern, pulse rate variability pattern, respiratory pattern and blood pressure patterns are analyzed at null steps or movement to detect movement data of sleeping, sitting and standing. The average speed of the emergency support apparatus is compared to human physical limit to compute movement data of cycling and driving. The speed at step movements and heart rate pattern are analyzed to compute movement data of walking, running or sprinting. The emergency support apparatus is configured to learn the accelerometer values to recognize plurality of movement data comprising walking, running, sprinting, biking and driving. The vital signal data and the real impedance is analyzed to compute EI meter and to detect the fatigue condition and stress condition. The subjective stress levels thresholds are stored and detected from the user markups. The blood sugar values are analyzed to compute hypoglycemia and hyperglycemia conditions. The heart rate pattern, neural parameters (i.e. autonomous neural activity coefficients and parameters), respiratory pattern and impedance data (i.e. from AC signal response) are analyzed to detect congestive heart failure. The decreasing SpO2 pattern, fast respiratory rate pattern and increased heart rate pattern is analyzed to detect CO poising condition. The low SpO2 data, fast unsteady breathing rate pattern and decreasing heart rate pattern is analyzed to determine hypoxia, hypoxiemia and blood disease. The reducing pulse rate pattern, reducing temperature and HRV pattern are analyzed to determine hypothermia condition. The increasing pulse rate pattern, increasing temperature pattern, increasing unsteady breathing pattern and HRV pattern are analyzed to recognize hyperthermia condition. The real impedance data is analyzed to recognize anxiety and seizure state. The response signals of the electrical biosensors set and optical biosensors set are applied as feedback to rectify errors and accurately compute the plurality of real-time biological information and clinical emergency conditions. Further an unsupervised learning is applied to the vital signal data to remove errors due to circadian cycle and to compute the circadian cycle health. On recognizing any of the life-threatening emergency or clinical emergency conditions, the emergency support apparatus alerts the life support network.

The emergency support apparatus includes a pressure sensor set to extract real-time pressure information, force of removal and emergency/abduction range. The emergency support apparatus in befit embodiment forms are suited to extract the method and force of removal and to indicate whether the emergency support apparatus is aggressively unstrapped by a victimizer.

The emergency support apparatus is configured to create a SWARM network through bluetooth antennae and wireless antennae set to interact with the life-support network through other intermediate wireless SWARM smart devices. The movement information (like the location, speed, etc) are extracted through the wireless antennae. The plurality of real-time biological information, pressure sensor data and movement data are analyzed by the emergency support apparatus to track the kidnapper's pattern and the impact of abduction. The emergency support apparatus includes a power supply unit comprising power management unit, USB charging module and supercapacitor-Battery set for the powering the apparatus. The emergency support apparatus has an additional renewable power supply unit set of supercapacitor-energy harvesting module. The display, accessorial devices, pressure sensor, 6/9-axis accelerometer, video camera, micro-mic and other electronics (like buttons, potentiometer) of the emergency support apparatus are used to operate it and access the in-built application. The apparatus emergency support apparatus records the emergency and abduction incidents through micro-mic and video camera module.

The analysis, computation and storage of the plurality of tracking information as well takes place through a central server, a network of accessorial devices operated by the user and the life-support network. The analysis, computation and storage through network of accessorial devices, central server and the life-support network improves overall efficiency and speed of emergency support.

Second Aspect

In second aspect, course of action on trigger of trigger commands and the ways to trigger the trigger commands and communicate the tracking information are explained. The emergency support apparatus is synchronized to a central server and a life-support i.e. a network of life-support network devices operated by SOS network, parent or guardian and social network of the user. The life-support network (i.e. network of life-support devices) can trigger and broadcast the trigger commands through their life-support network application interface. The emergency support apparatus or any accessorial mobile devices used by the user (i.e. primary network) can trigger and broadcast the emergency or alert command through a user application interface. The communication between the primary network and the life-support can takes place through the central server present in the routing pathway. The central server stores and transfers the tracking information between the primary network and the life-support network. The communication can also take place directly through the wireless network of Bluetooth, WLAN, mobile communication system (GSM) and SWARM network. The SWARM network is established as an alternative intermediate communication pathway or communication routing pathway. The primary network, life-support network and/or the central server is configured to compute shorter and robust intelligent pathways for communicating the tracking information and trigger commands. The robust and shortest pathways is utilized as an efficient and faster means to transfer the tracking information and trigger commands between the primary network and the life-support network.

The primary network, life-support network or the central server automatically processes user data, wherein configured to:
- analyze the pressure sensor set to extract a live and a recorded pressure data;
- analyze and validate the pressure sensor set to recognize the method and the force of removal of the emergency support apparatus;
- to validate the status of the wireless antenna set, bio-sensors and other sensors of the emergency support apparatus;
- to check the status of the wireless networks of the emergency support apparatus;
- to deduce shortest and robust communication wireless path;
- to validate if the bio-signal data from the biosensor set is within the realistic threshold value; and
- to analyze the biosensor set to verify the status of the emergency support apparatus such as 'if the wearable/emergency support apparatus is worn' and 'does the data approximately correlate with the individual'.
- to analyze and process global positioning system (GPS) Unit for inferring location data, speed of the emergency support apparatus and communication pathway;
- to analyze and process WLAN for inferring network data, location data and communication pathway;
- to process Bluetooth for SAWRM devices enabled communication pathway;
- to process Bluetooth for inferring the network device information, network device location data and proximity of the primary apparatus (i.e. emergency support apparatus);
- to analyze and process accelerometer to track the mode of transport and phase of the apparatus; and
- to analyze and process the biosensor set to compute pulse rate, breathing rate, oxygen saturation, psychological stress, neural activity, blood pressure data, blood sugar levels and other important health data of the user.

An automatic emergency triggering, wherein configured:
- to verify the pressure sensor for valid abduction range and realistic range;
- to the pressure sensor data to recognize the method of removal, force of removal and other information (i.e. whether the emergency support apparatus is aggressively unstrapped by the victimizer);
- to validate if bio-signal data is in the realistic range and if the device (i.e. emergency support apparatus) is worn by the user;
- to verify if the recorded bio-signal data is in the range of pre-clinical or abduction emergency (i.e. plurality of real-time clinical emergency conditions that includes hypoglycemia state, hyperglycemia state, congestive heart failure condition, CO poisoning condition, hypoxia condition, hypothermia condition, hyperthermia condition, stress condition, anxiety condition seizure condition, sleep apnea, etc); and
- to alert the life-support network automatically on identification of the user's life at risk (i.e. due to the pressure data indicating abduction range or bio-signal data indicating clinical emergency conditions).

The plurality of real-time tracking information can be accessed and viewed on both the primary network and the life-support network (i.e. through their application interface). Further, a missing note can be sent from parent's/guardian's device and SOS device to the life-support network and other network devices in the vicinity (of emergency support apparatus).

The network of life-support devices are preferably mobile devices operated by the life-support network. The network of life-support devices being preferably mobile devices can view and operate the trigger commands through buttons on application such as child tracking applications and clinical emergency applications through their display as described in the later aspects. These devices operated by the life-support network can also be other computer implemented means that have suitable display to view the real-time tracking and button or keys to operate the trigger commands.

Third Aspect

In the third aspect, a child tracking application synchronized to the emergency support apparatus and life-support network is described. The child tracking application has two modules of parenting care application and life-support network application, which are wirelessly synchronized with the emergency support apparatus (i.e. the primary real-time apparatus). The application is used by life-support network and user through their devices i.e. that preferably would be a mobile device or a computer or equivalents. The application has two trigger commands, wherein said trigger commands are emergency command and alert command. The trigger of emergency command alerts and communicates the tracking information to the life-support network. The trigger of alert command alerts and communicates the tracking information to the life-support network and the plurality of network devices in the vicinity/near-by the location of emergency. The emergency and alert commands are triggered through the parenting care application, the real-time primary apparatus (i.e. the emergency support apparatus) and the life-support network. The application module has a missing note functionality for disclosing more particular information about the user (as mentioned earlier it sent from the SOS network or guardian/parent device). The user's personal information (of age, gender, description, etc) and real-time tracking information on location, transportation speed, transportation mode, map data, medical data (of pulse rate, oxygen saturation, breathing rate, psychological stress, neural activity, blood pressure data, blood sugar levels, etc), biological condition and device status (of device attachment status, force of removal and unbuckling method) are displayed on the child tracking application. A live vital information monitor is available on the synchronized devices (i.e. through their child tracking application) for viewing the live medical information (i.e. detailed live biological signals). On automatic recognition of abduction events or clinical emergency conditions (i.e. through pressure sensor or biosensors set of the emergency support apparatus) or on triggering emergency/alert command through the application, the application alerts the life-support network with an abduction alert, real-time tracking information and missing note (as mentioned earlier the missing note is recorded by the parent/guardian or SOS network).

The network of life-support devices are preferably mobile devices operated by the life-support network. The network of life-support devices being preferably mobile devices can view and operate the trigger commands through buttons on the child tracking application through their display. These devices operated by the life-support network can also be other computer implemented means that have suitable display to view the real-time tracking and button or keys to operate the trigger commands.

Fourth Aspect

A clinical emergency application is explained in the fourth aspect of the invention. The clinical application comprises of user application and a network of life-support devices based client end application, which are wirelessly synchronized with the primary apparatus (i.e. the emergency support apparatus). The application has an "alert network" trigger command to alert the life-support, "alert SOS" trigger command to alert the SOS network, and an "alert all" trigger command to alert the devices in the vicinity network (i.e. of the emergency support apparatus), personal network (i.e. devices operated by parent/guardian and social network) and SOS network. The application has an automated description on diagnosed and predicted medical condition for disclosing more particular information on the present user condition. The user's personal information (of username, age, gender, description, medical insurance number and medical plan), and real-time information on location, transportation speed, transportation mode, map data, diagnosed medical condition, predicted medical condition, medical data (of pulse rate, oxygen saturation, breathing rate, psychological stress, blood pressure data and blood sugar levels), biological conditions and device status are displayed on the user application and client application. A live vital information monitor is available on the synchronized devices for viewing the live medical information (i.e. detailed live biological signals). On recognized events of emergency (i.e. through the pressure sensor or the biosensors set of the emergency support apparatus) or on manually triggering the trigger commands (i.e. through application), the application alerts the life-support network with medical emergency alert and real-time tracking information.

The network of life-support devices are preferably mobile devices operated by the life-support network. The network of life-support devices being preferably mobile devices can view and operate the trigger commands through buttons on the clinical emergency application through their display. These devices operated by the life-support network can also be other computer implemented means that have suitable display to view the real-time tracking and button or keys to operate the trigger commands.

Fifth Aspect

The fifth aspect of the disclosure explains the working of a network of accessorial devices synchronized to the real-time emergency support apparatus. The accessorial devices are wirelessly synchronized with the emergency support apparatus. The trigger commands, the emergency support apparatus and its embodiment forms, and in-built applications are operated through the accessorial mobile devices. The accessorial mobile devices computes and stores the real-time data and the recorded tracking information. The real-time tracking information and recorded data are viewed on the display of the accessorial mobile device and emergency support apparatus. The accessorial mobile device includes a touch display to operate the emergency support apparatus, to trigger the commands and to access the in-built applications. The accessorial mobile device further comprises a video camera and a mic, which captures and records the emergency events. The accessorial mobile devices communicates the real-time and recorded tracking information to the life-support network. The video camera and mic are used to operate the device and the in-built applications. The speaker and the display of the accessorial device are used for perceiving the life-support network's responses and real-time tracking data.

Sixth Aspect

In the sixth aspect, a child tracker embodiment of the real-time emergency support apparatus is described. The child tracking apparatus has a belt buckle with inbuilt pressure sensor set to keep track of the pressure on the device. The upper buckle element of the child tracker is made of magnetically attractable element and has an inbuilt pressure sensor. In particular, the pressure sensor is embedded on the inner surface of the magnetically attractable buckle element. The lower magnetic buckle element and upper buckle element are held together through a spring hinge. The magnetic attraction between the buckles and clutching action of the hinge along with a belt is used to fasten the device securely on the user. The belt is made of up of cloth with inner foam base/sponge-like material to avoid motion errors in the recording. The pressure sensor of the child tracking apparatus keeps track of the pressure on the device, and method and force of device removal. The belt has tail end with stickable pad and adhesive surface, which is additionally used for fastening the device. The apparatus has a heat regulating case that contains electronics, biosensor front-end with plurality of biosensors, which is kept in contact with the child for extracting real-time medical data. The real-time medical information extracted by biosensors, wireless antennae data, movement data extracted by accelerometer and recorded location data are used for inferring the present condition of the user.

The pressure sensor set is intentionally placed in aforementioned spot of the aforementioned embodiment so as the victimizer can be tracked without user involvement. The befit placement of pressure sensor or pressure sensor set in the aforementioned embodiment inclines the victimizer as a medium to activate the trigger command and to alert life-support network without the interference or involvement of the user. Therefore, the risk for the user would be minimized for the user as the user may alone not get involved in the process of requesting for emergency support.

Seventh Aspect

A wearable emergency support apparatus with a round contact surface is described in the seventh aspect of the invention. The round contact surface is used as a means to evade cuts and injuries, that may otherwise occur due to the sharp edges (i.e. that could happen during victimizer attacks). The round wearable frame of the wearable emergency support apparatus contains a pressure sensor, biosensor set and other electronics. The pressure sensor and the biosensors are embedded on the contact side of device frame, which is utilized to record the pressure and real-time biological data. An additional pressure sensor, affixed on the detachable buckle element at the rear end of the front strap, is used to track the force of aggressively unstrapping the device. The apparatus is fastened by attaching back strap with adjustment holes to the detachable buckle with tongue and free-loop on the front strap.

The pressure sensor set is intentionally placed in aforementioned spots of the aforementioned embodiment so as the victimizer can be tracked without user involvement. The befit placement of pressure sensor or pressure sensor set in the aforementioned embodiment inclines the victimizer as a medium to activate the trigger command and to alert life-support network without the interference or involvement of the user. Therefore, the risk for the user would be minimized for the user as the user may alone not get involved in the process of requesting for emergency support.

Eighth Aspect

In the eighth aspect, a four-pressure based smart wearable emergency apparatus is described. The wearable apparatus has 4 pressure sensors placed at the four corners of the smart wearable frame, so that the pressure on the user can be accurately extracted over a single central pressure sensor. The four-pressure configuration gives information on the direction of unstrapping, force of removal and more. The plurality of biosensors and other sensors are placed on the contact surface of the rounded corner device frame for tracking the real-time biological data. The device frame with rounded corners on the wearable apparatus evades cuts and injuries (i.e. that could happen during victimizer attacks). The device has a front strap with a free-loop and a fixed magnetically attractable buckle element, and a back strap with a movable magnetic clasp. The wearable apparatus is fastened on the wrist or other body parts by inserting the back strap through magnetically attractable buckle element and free-loop, until the movable clasp of the back strap is magnetically attracted to the magnetic element. A stopper is affixed on the back strap to prevent the slipping of the movable magnetic clasp from the strap.

The pressure sensor set is intentionally placed in aforementioned spots of the aforementioned embodiment so as the victimizer can be tracked without user involvement. The befit placement of pressure sensor or pressure sensor set in the aforementioned embodiment inclines the victimizer as a medium to activate the trigger command and to alert life-support network without the interference or involvement of the user. Therefore, the risk for the user would be minimized for the user as the user may alone not get involved in the process of requesting for emergency support. In this case, extra information on the direction of removal can be used to infer further information on the pattern of the victimizer, and accordingly the efficiency of the current embodiment can be improved through a combination of the current embodiment with said earlier embodiments as described in the sixth and seventh aspect.

Ninth Aspect

The ninth aspect explains an accessorial emergency support apparatus with video camera and microphone. The accessorial emergency support apparatus has embedded high definition video camera and microphone, which secretively tracks and records the events of emergency. The video camera and microphone are used to operate the device (i.e. the accessorial emergency support apparatus) and its in-built applications. The accessorial emergency support apparatus has a hardware box packaged with electronics, which comprises of a central microprocessor with internal memory, wireless antennae set, user interaction components and other essential internal circuitry components. The microcontroller with internal memory of the device is attached to wireless antenna set of WLAN module, Bluetooth module, GPS module and GSM module which is utilized for wirelessly communicating the real-time and recorded data to the wireless life-support network and the primary network. The GPS and the wireless antennae set are additionally used to track the speed and location of the device (i.e. the accessorial emergency support apparatus). The accessorial emergency support apparatus has 9/6-axis accelerometer, which tracks movement signals and acts as a real-time feedback for noise cancellation. The accessorial emergency support apparatus is attached to a power supply unit comprising of PMU, micro-USB module, supercapacitor-battery set and the supercapacitor-energy harvester for powering and managing the power supply. The accessorial emergency support apparatus has a detachable adhesive surface on the top or bottom surface, that is utilized to attach and mount it on the primary emergency support apparatus. The video camera based accessorial emergency support apparatus further comprises of a power button and wireless button for operating the device, synchronizing the data and for powering on and off the device.

DETAILED DESCRIPTION OF THE INVENTION

Comprehensively, the disclosure can be utilized and perceived in various applications that include medical instruments, health management gadgets, anti-abduction devices, parenting-care devices, service personnel protection technology, accident prevention devices and other forms of emergency support apparatuses. The principle of the described invention is not intended to limit to the specific device, system and software application.

Figure 1:
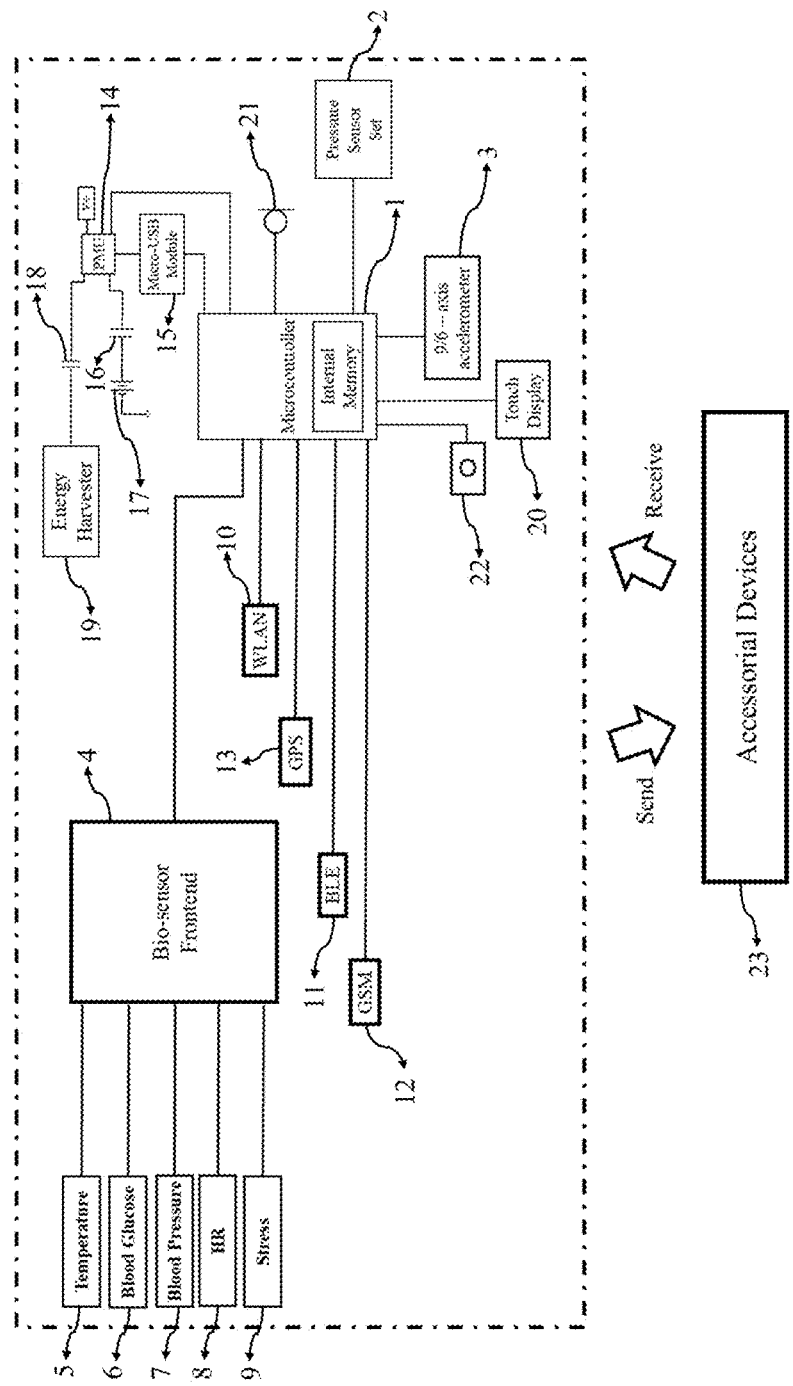
FIG. 1 describes general electronics block diagram and general hardware architecture of the emergency support apparatus.

FIG. 1 is the hardware block diagram of the emergency support apparatus. The microprocessor with inbuilt memory 1 of the emergency support apparatus communicates with the sensor frontend, sensors and other digital components. The microprocessor 1 internally computes and stores the data. The pressure sensor set 2 attached to the microcontroller 1 extracts the real-time pressure data. The pressure sensor set 2 extracts force and method of unbuckling/unstrapping of the emergency support apparatus placed in befitted spots of the emergency support apparatus (as described in FIG. 4, FIG.5 and FIG. 6). This pressure sensor set 2 can indicate event of aggressively unstrapping or unbuckling by a victimizer, when placed in suitable spots of an embodiment as described in the child tracker apparatus embodiment form (as in FIG. 4), and in wearable embodiment forms (as in FIG. 5 and FIG. 6). The pressure sensor set 2 can also indicate such event through direction of removal when placed in suitable spots as described in wearable embodiment forms (as in FIG. 6). The accelerometer 3 extracts the real-time movement feedback and the motion data. The flowchart for to eliminate movement errors in the recordings and to extract plurality of movement data are explained below (in set of FIG. 3). Temperature sensor 5, Blood glucose sensor 6, Blood Pressure Sensor 7, Pulse sensor 8 and Stress sensor 9 attached to Bio-sensor front-end 4 extracts the real-time biological and health information. Wireless antennae set of WLAN 10, BLE 11, GSM 12 and GPS 13 transfers the tracking information between emergency support apparatus and as well as the network of accessorial devices 23 (that includes accessorial mobile devices used by the user and life-support network i.e. plurality of devices operated by the life-support network). The wireless antennae set of 10-11-12-13 are also utilized to track the location and the speed of the device (i.e. the emergency support apparatus). The Bluetooth antennae 11 and other wireless antennae set 10-12-13 creates a SWARM network and shorter pathways through the intermediate smart devices of wireless SWARM devices to interact with the network of devices 23. This SWARM network based wireless technology can enable communication even when there is no access to standard internet, mobile or satellite communication channels. The network of accessorial devices 23 are as well used as an efficient and faster means to compute and store the information externally. The analysis, computation and storage of the plurality of tracking information as well takes place through a central server, and the network of accessorial devices 23, which increases overall efficiency and speediness of emergency support. The pressure sensor 2, bio-sensor set 5-6-7-8-9, accelerometer 3, and 10-11-12-13 are utilized to extract the kidnapper's pattern, the impact of abduction, seriousness of the emergency condition and other information. The emergency and abduction events are perceived through the video camera module 22 and micro-mic module 21. The real-time and recorded information are viewed on the display 20. The touch display 20 is utilized to operate the emergency support apparatus, access the in-built applications and the real-time system. The touch display 20, accessorial devices 23, video camera module 22, pressure sensor 2, 9/6-axis accelerometer 3, micro-mic 21 and other electronics like buttons, potentiometer are used by the user to interact with the device (i.e. emergency support apparatus), and to operate the device (i.e. emergency support apparatus) and its in-built applications. The power supply unit of the emergency support apparatus comprises Power management Unit (i.e. PMU) 14, USB module 15, set of Supercapacitor 16—Battery 17 and a renewable power set of Supercapacitor 18—Energy Harvesting Module 19. The power supply unit powers and manages power supply to the emergency support apparatus. The power supply unit alleviates the problems in an emergency situation where the emergency support apparatus runs of power due to typical battery source draining, operating cycles and environmental conditions.

Figure 2:
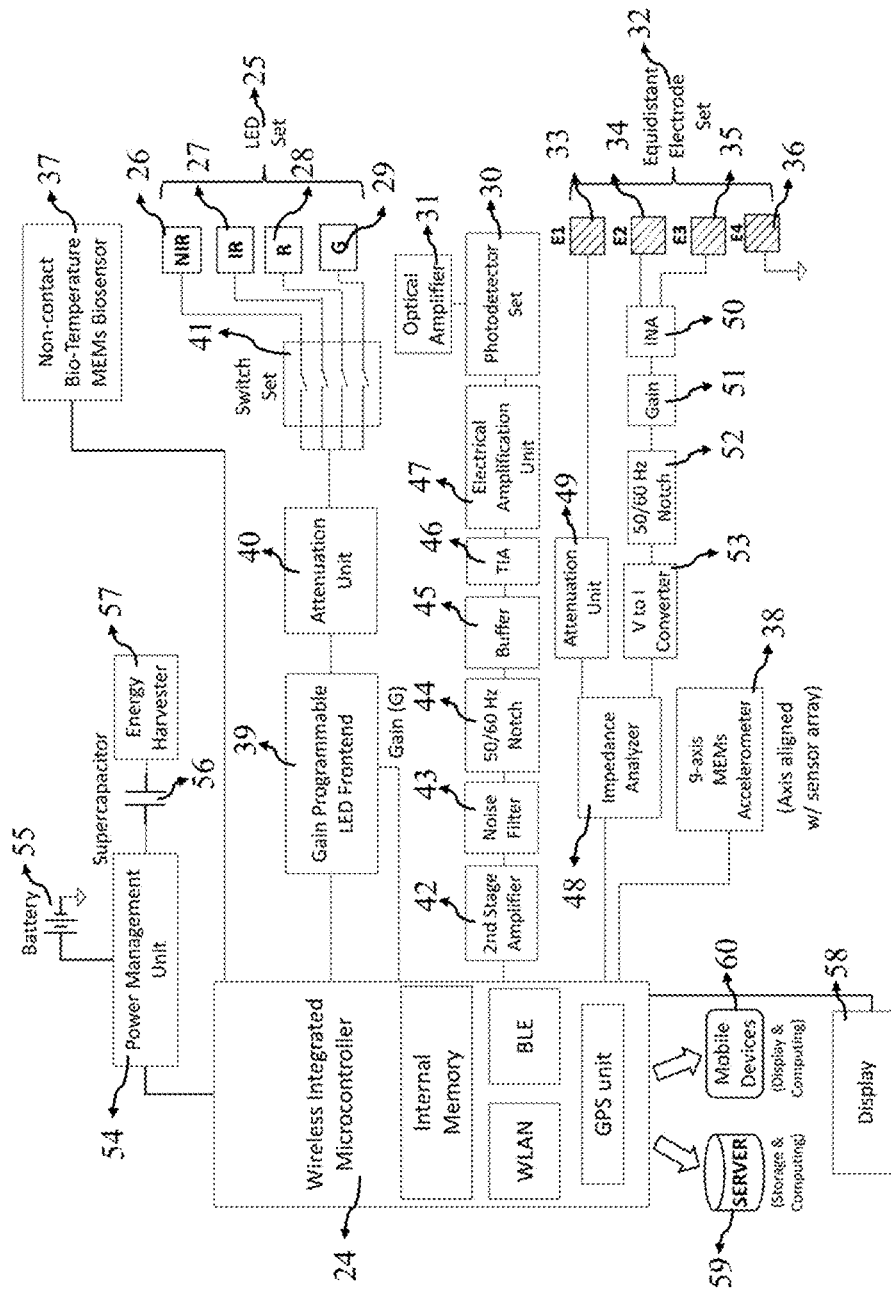
FIG. 2 describes the preferred low-powered biosensing hardware architecture of the emergency support apparatus.

FIG. 2 is the preferred low-powered biosensing hardware architecture of the emergency support apparatus. The hardware of the emergency support apparatus in preferred architecture comprises a wireless integrated microcontroller with internal memory 24 comprising BLE, WLAN and GPS antennae. The preferred hardware architecture of the emergency support apparatus for biosensing comprises an optical biosensors set comprising green (G) LED 29, red (R) LED 28, infrared (IR) LED 27, near infrared (NIR) LED 26 and photodetector set 30, an electrical biosensors set 32 comprising four electrical sensors E1 33-E2 34-E3 35-E4 36, a non-contact temperature biosensor 37, a 9-axis accelerometer 38 and plurality of accompanying biosensor frontend and processing components. The microcontroller 24 communicates with the sensor frontend, sensors, digital components and enables wireless communication to external devices 23-59-60, and also computes and stores the tracking information. The plurality of real-time biological information and clinical emergency conditions i.e. heart rate, pulse rate variability, oxygen saturation, neural activity, breathing pattern, blood pressure levels, blood sugar levels, body temperature, sleep cycles, sleep apnea condition, hypoglycemia state, hyperglycemia state, congestive heart failure condition, CO poisoning condition, hypoxia condition, hypothermia condition, hyperthermia condition, stress condition, anxiety condition and seizure condition are extracted from the bio-signals obtained from at least one or more of the biosensor LED set 25 comprising green (G) LED 29, red (R) LED 28, infrared (IR) LED 27, near infrared (NIR) LED 26 and photodetector set 30, and electrical biosensors set 32 comprising four electrical sensors E1 33-E2 34-E3 35-E4 36, and non-contact temperature biosensor 37. The preferred hardware architecture of the emergency support apparatus comprises 9-axis accelerometer 38 whose axis is aligned with the biosensors set 25-26-27-28-29-30-31-32-33-34-35-36-37. The signals from 9-axis accelerometer 38 are correlated as a real-time feedback with the bio-signals from the biosensors set to remove movement errors in the bio-signals from the biosensors set. The plurality of movement data and user condition comprising sleeping, sitting, standing, moving, walking, running, sprinting, step movements, biking and driving are extracted from accelerometer 38. The flow diagrams to compute the plurality of movement data, the plurality of biological information and clinical emergency conditions and the movement error free bio-signal are described in the series of FIG. 3A to FIG. 3J.

The low powered and safe operation of the preferred hardware architecture of the emergency apparatus is further ensured through the inputs from the emergency support apparatus to the set of green LED 29, red LED 28, infrared LED 27, near infrared LED 26 reduced through an attenuation circuit 40 integrated at the LED frontend and the optical amplifier 31 improving amplification of the optical bio-signals responses at the photodetector set 30. The multi-spectral signals from green LED 29, red LED 28, infrared LED 27, near infrared LED 26 are generated based on the control commands through a gain programmable LED Frontend 39 and a switch set 41. The switch set 41 along with gain programmable LED Frontend 39 enables operation of multiple LEDs (26-27-28-29) through a single LED frontend 39 and attenuation circuit 40, which further makes the hardware of the emergency support apparatus low-powered and compact. The low-powered optical response signals recorded at the photodetector set 30 is suitably amplified, stabilized, filtered of noise, converted and processed through a series of processing circuit components of 47-46-45-44-43-42. The microprocessor 24 is connected an impedance analyzer IC 48 that injects a low-powered AC signal through an attenuation circuit 49 connected to an electrical sensor E1 33 of the electrical biosensors set (E1-E2-E3-E4) and the low powered AC signals are drained through the electrical sensor E4 36 of the electrical biosensors set (E1 33-E2 34-E3 35-E4 36). The biosafety of the biosensing design is ensured through the attenuation circuit 49. The bio-signal data of real and imaginary impedances of AC response electrical bio-signals are extracted through the impedance analyzer IC 48 connected to a series of response processing circuits 50-51-52-53 attached to the two electrical sensors E2 34-E3 35 of the electrical biosensors set that are placed between the other two electrical sensors E1 33-E4 36 of the electrical biosensors set. The AC response electrical bio-signals are extracted, amplified, stabilized, filtered of noise and converted through the series of processing component 50-51-52-53. The emergency captures the real-time temperature signals through the non-contact temperature biosensor 37. The hardware of the emergency support apparatus is powered by both battery 55 and external renewable energy harvester 57—supercapacitor set 56 connected to the power management unit 54. The external renewable energy harvester 57—supercapacitor set 56 is an alternative powering unit. The hardware of the emergency support apparatus can also include a set of battery and supercapacitor as described above in the general hardware architecture (i.e. Supercapacitor 16—Battery 17), which would extend the lifecycles and operability conditions of the power supply unit. The emergency support apparatus can further wirelessly communicate through the wireless antennae to compute the plurality of tracking information through distributed computational architecture of internal micro-computer 24, server technology 59 and other network mobile devices 60 (as in case of above described general hardware architecture could be 23 that includes the life-support network and network of accessorial devices). The hardware of the emergency support as described above can further include video camera module and micro-mic module to record and perceive emergency and abduction events. The real-time tracking information can viewed and accessed through the display 58. The preferred hardware architecture further includes the pressure sensor set 2 as described above and embodied in befit embodiment forms to compute the plurality of pressure sensor set data. The pressure sensor set in combination with biosensors set 25-26-27-28-29-30-31-32-33-34-35-36-37 and the 9-axis accelerometer 38, can extract the kidnapper's pattern, the impact of abduction, seriousness of the emergency condition and other information. The touch display, network of accessorial devices, video camera module, pressure sensor, 9-axis accelerometer, micro-mic (and with other electronics like buttons, potentiometer) can be used by the user to interact with and operate the emergency support apparatus and its in-built applications.

Figures 3A, 3B:
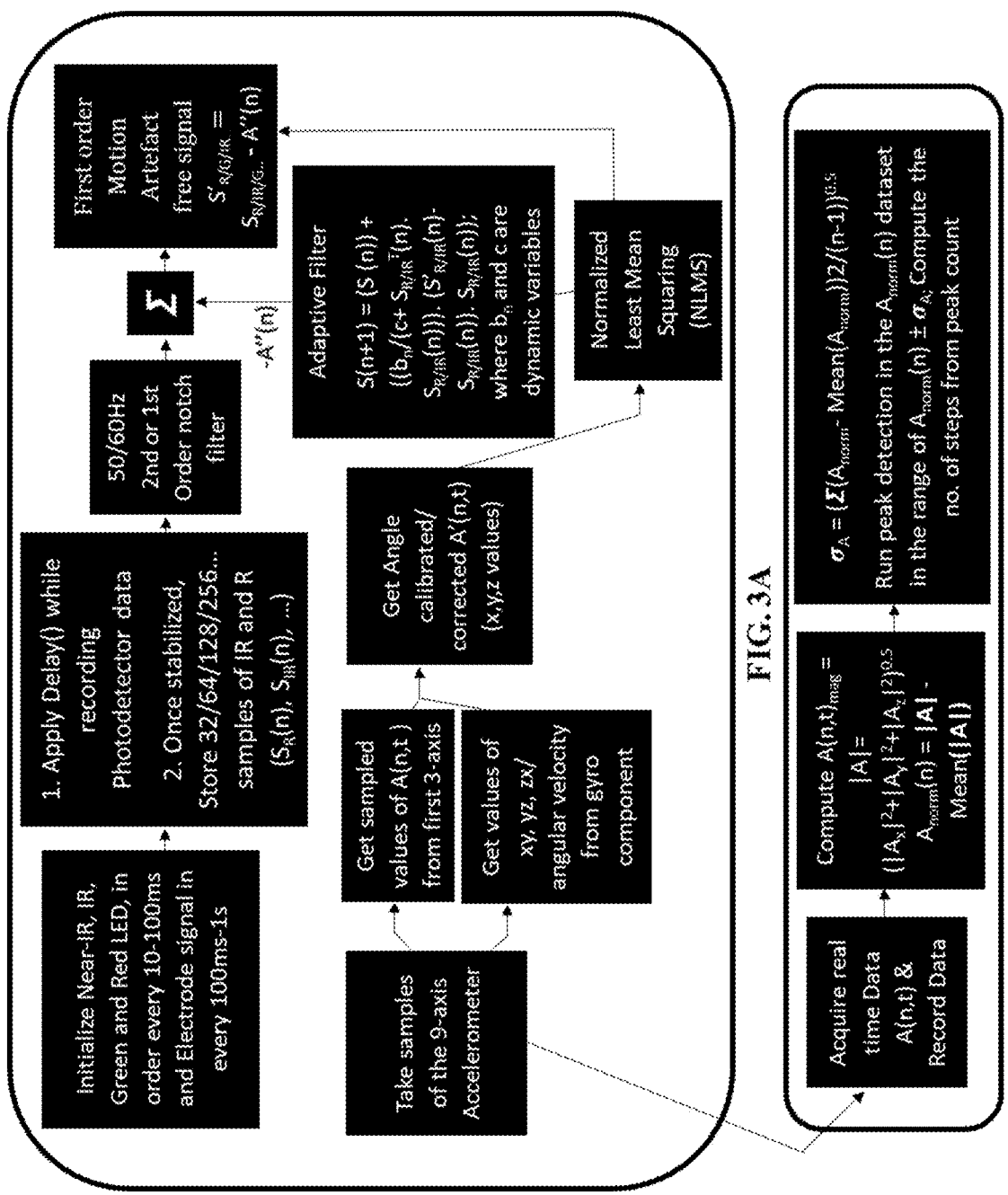
FIG. 3A to FIG. 3J describes the flow diagrams to extract movement error bio-signals, plurality of real-time biological information, plurality of clinical emergency conditions and plurality of movement data from the emergency support apparatus.

FIG. 3A describes the flowchart to configure accelerometer as real-time feedback to remove movement errors from bio-signals extracted from the biosensors set. The signals from the 9-axis accelerometer 38 (or 3) are recorded along/parallelly with bio-signals data from biosensors set (i.e. optical and electrical biosensors of 25-26-27-28-29-30-31-32-33-34-35-36-37) in their respective sampling rate with a delay. Initially the bio-sensing samples from the biosensors set may be recorded on stabilization before the correlation. The sampled bio-signals are initially passed through a 50/60 Hz digital notch filter to remove the power line noise disruption. The accelerometer signals are calibrated with their angular values obtained from the gyro component to compute angle calibrated accelerometer signals. The angle calibrated accelerometer signals, the recorded bio-signals post the notch filtering and the delay are analyzed, correlated and processed with a normalized parameters based adaptive filter or repetitive adaptive filter to remove movement errors ($A''(n)$) from the bio-signal data. A first order noise free real-time bio-signals ($S'(n)$) are obtained at the end of the analysis and computation as described in FIG. 3A. Correlation can be similarly applied to remove errors from the bio-signals of the biosensors set. Also, suitably correlation can further improved through the rest of the components of the 9-axis accelerometer.

FIG. 3B explains the flowchart to configure the accelerometer to obtain step movements and number of steps. (Described in FIG. 3I to FIG. 3J to differentiate between step movements and non-step movements and to classify the user movement or to identify the mode of transportation). The various axis values of the parallelly recorded accelerometer signals are analyzed to obtain step movements or movement data. A root of squares of individual axes values of (i.e. $A_x$, $A_y$ and $A_z$) of the accelerometer signals are computed and their mean dataset is computed. A normalized values dataset of the accelerometer signals are further computed through a difference between said root of squares of individual axes values of (i.e. $A_x$, $A_y$ and $A_z$) of the accelerometer signals and said mean dataset. The axis values may well be further normalized before suitably through calibration of the parameter obtained from the rest of the components of the accelerometer signals. The deviation of the normalized values dataset of the accelerometer signals is computed and recorded. The dataset of the normalized values dataset of the accelerometer signals within the deviation of the normalized values dataset of the accelerometer signals is analyzed for peaks to compute the step movements and number of steps. Suitably other ways to remove baseline errors may be applied before computing statistical data analysis or deviation computation.

Figure 3C:
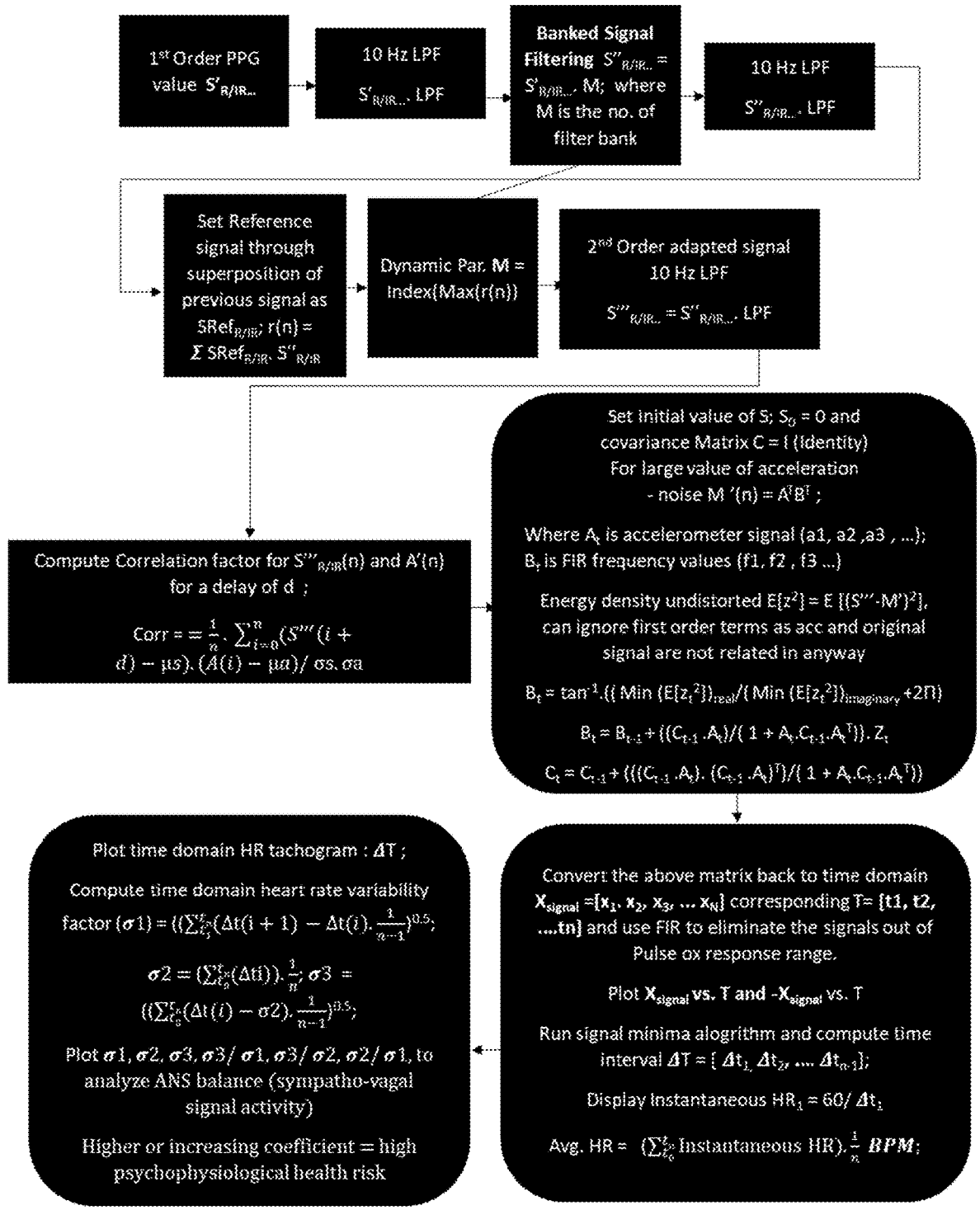

FIG. 3C is the flow-diagram wherein the bio-signals from the biosensors set and accelerometer are processed correlated to further remove noise and movement errors in the bio-signals obtained from the biosensors set and as well to compute neural activity parameters, instantaneous heart rate, avg. heart rate and HR tachograph. The recorded real-time bio-signals of the biosensors or the obtained first order noise free real-time bio-signals are analyzed and processed through a banked signal filtering, wherein the bio-signals are sent passed through iterative banked signal filters with dynamic parameter (M). This dynamic parameter adjusts according to the initial bio-signals and bio-signals obtained post the analysis through the banked signals filters. The real-time bio-signals i.e. the first order bio-signals or otherwise the bio-signals from the bio-sensor can be passed through a series of digital filter to remove errors associated with the bio-signals such as high or low frequency noise. A second order noise free real-time bio-signals of the biosensors set are obtained after analysis of real-time bio-signals through the banked signal filtering. The second order noise free bio-signals or otherwise the real-time bio-signals from the biosensors set, the accelerometer signals (or angle calibrated accelerometer signals) and a delay are correlated to obtain a correlation factor (Corr). The correlation factor can be applied to remove the movement errors in the bio-signals. For large values of acceleration, a movement noise matrix ($M'(n)$) is computed by correlating (i.e. through matrix operations) the real-time accelerometer values and the finite impulse response (FIR) of the real-time bio-signals from the biosensors set or otherwise first or second or third order noise free bio-signals. Undistorted energy of the real-time bio-signals is computed after removal of the movement errors through the movement noise matrix operation. At this stage an uncompromised dataset of the real-time bio-signals data from the biosensors set in different frequency spectrum are computed that is free from movement errors and other source noises. The real-time amplitude signal dataset ($X_{signal}$) and their respective time frame dataset (T) of the noise free real-time bio-signals are recorded. A FIR may be additionally applied to the dataset remove out of response bio-signals. The real-time amplitude signals dataset with respect to its time frame dataset are plotted to obtain detailed live signals of the noise free bio-signals. The extremum i.e. maxima and minima of the real-time amplitude signal dataset ($X_{signal}$) are analyzed and time intervals dataset ($\Delta T$) between the extremum are computed. The time intervals dataset are analyzed to compute instantaneous heart rate and the average heart rate. The time intervals dataset are plotted to obtain a HR tachograph. A pulse rate variability or heart rate variability factors of these time intervals dataset are analyzed to compute a plurality of autonomous neural activity coefficients of $\sigma 1$, $\sigma 2$, $\sigma 3$, $\sigma 3/\sigma 1$, $\sigma 3/\sigma 2$, $\sigma 2/\sigma 1$. As described in the figure FIG. 3C, $\sigma 1$ is computed by taking root of average of difference between the adjacent time intervals of the time intervals dataset and $\sigma 2$ is computed average of the time intervals of the time intervals dataset and $\sigma 3$ is computed by taking root of the average of the difference between time intervals of the time intervals dataset and $\sigma 2$, and accordingly the $\sigma 3/\sigma 1$, $\sigma 3/\sigma 2$, $\sigma 2/\sigma 1$. These computed autonomous neural activity coefficients of $\sigma 1$, $\sigma 2$, $\sigma 3$, $\sigma 3/\sigma 1$, $\sigma 3/\sigma 2$, $\sigma 2/\sigma 1$ are assessed to analyze the Autonomous Neural System (ANS) Balance that indicates the sympatho-vagal signal activity and also risk associated with the psychophysiological system.

Figure 3D:
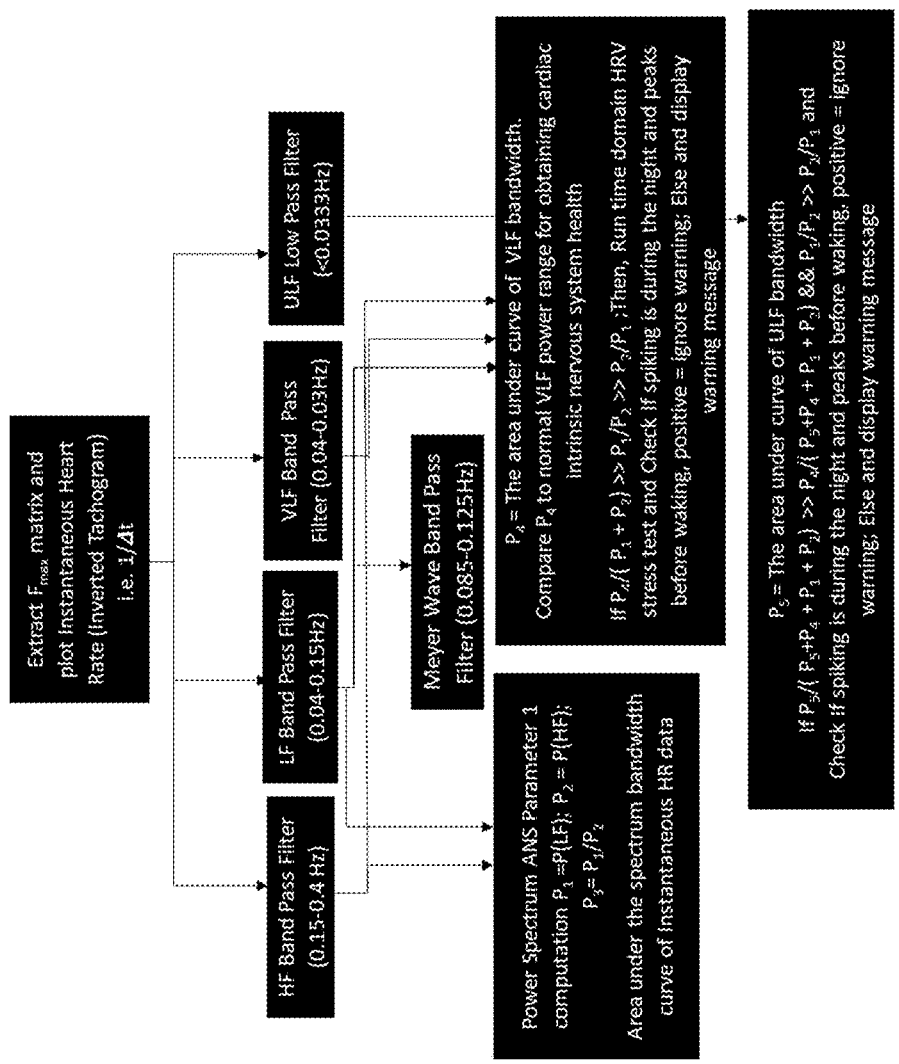

FIG. 3D describes the flow-diagram to extract autonomous neural activity assessment parameters from the real-time bio-signals. The computed noise-free real-time bio-signals from the biosensors set from FIG. 3C or the first order noise real-time free bio-signals from the biosensors set are separated into frequency spectrums of HF, LF, VLF and ULF by processing the bio-signals through a band pass filters of HF, LF, VLF and ULF. The separated real-time bio-signals in the bands of HF, LF, VLF and ULF are further analyzed for their power spectrum under their bands to extract autonomous neural activity assessment parameters of P1, P2, P3, P4 and P5. The power spectrum under LF of the real-time bio-signals is computed to obtain P1, the power spectrum under HF of the real-time bio-signals is computed to obtain P2, the ratio of P1 and P2 is computed to obtain P3, the power spectrum under VLF of the real-time bio-signals is computed to obtain P4 and the power spectrum under ULF of the real-time bio-signals is computed to obtain P5. The autonomous neural activity assessment parameters of P1, P2, P3, P4 and P5 and their ratios are compared to analyze the Autonomous Neural System (ANS) activity and other health problems.

Figure 3E:
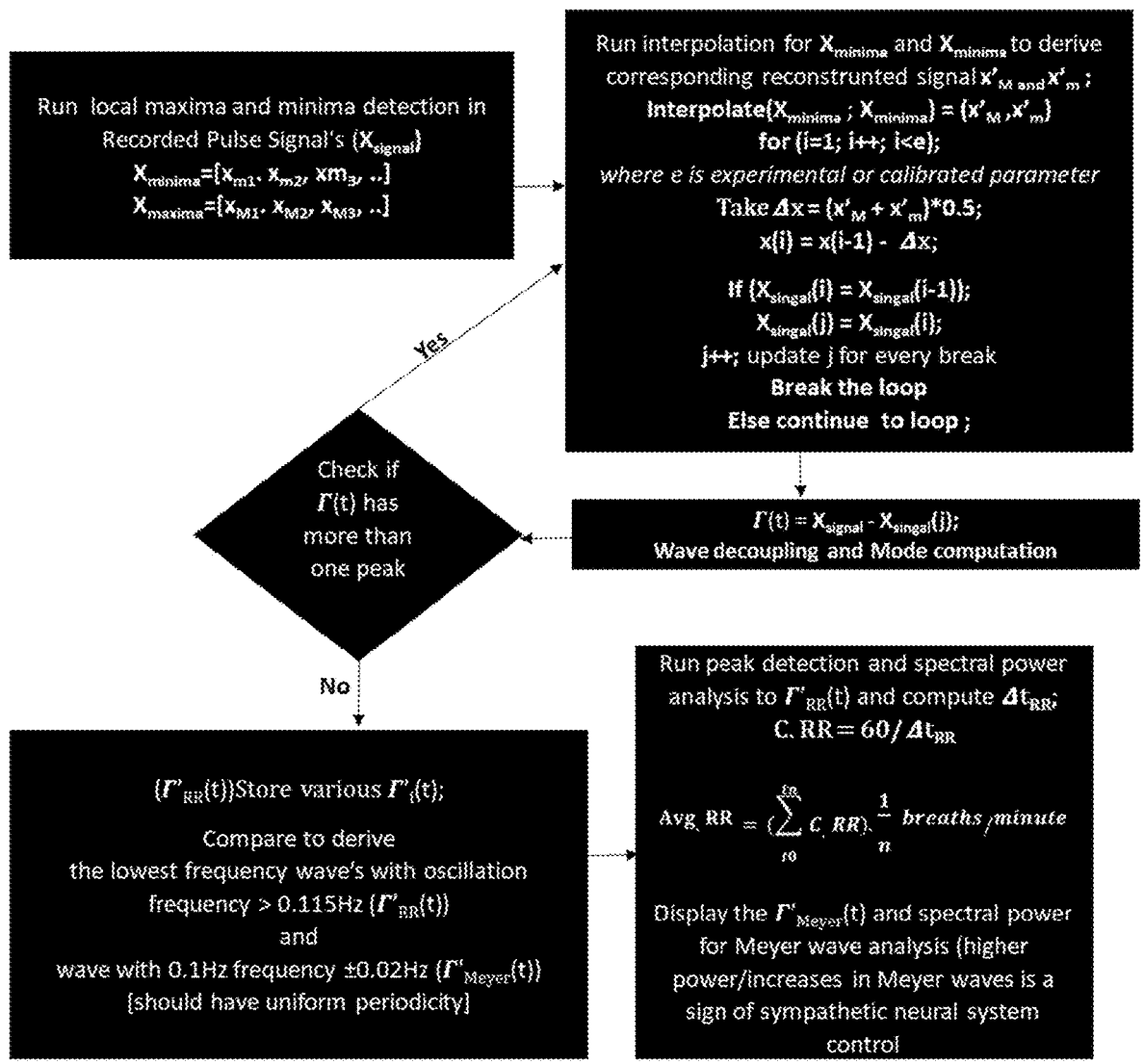

FIG. 3E describes the flow-diagram to compute real-time respiratory signals and respiratory rate from the real-time bio-signals. The local maxima and minima dataset of the noise free real-time bio-signals are recorded. The interpolated real-time values of recorded local maxima and minima dataset are analyzed against the noise free real-time bio-signals through iterative decoupling to decouple the real-time bio-signals. The decoupled wave ($\Gamma(t)$) are verified for one peak of extremum within the decoupled wave to obtain a decoupled real-time bio-signals. The decoupled real-time bio-signals (Γ(t)) is analyzed for frequency within the breathing signals range to obtain the real-time respiratory signals or decoupled real-time respiratory signals ($\Gamma'_{RR}$(t)). The real-time respiratory signals are analyzed to compute respiratory time intervals dataset ($\Delta t_{RR}$) between the peaks of the real-time respiratory signals. The continuous respiratory rate and average breathing are computed from the respiratory time intervals dataset of the real-time respiratory signals. Similarly, an analysis is run for frequency range within the meyer band to obtain real-time meyer wave signals ($\Gamma'_{Meyer}$(t)). The real-time meyer wave signals and spectral power within the meyer wave is analyzed to infer sympathetic neural action, wherein higher power or increase in meyer wave pattern is a sign of sympathetic neural system control.

Figure 3F:
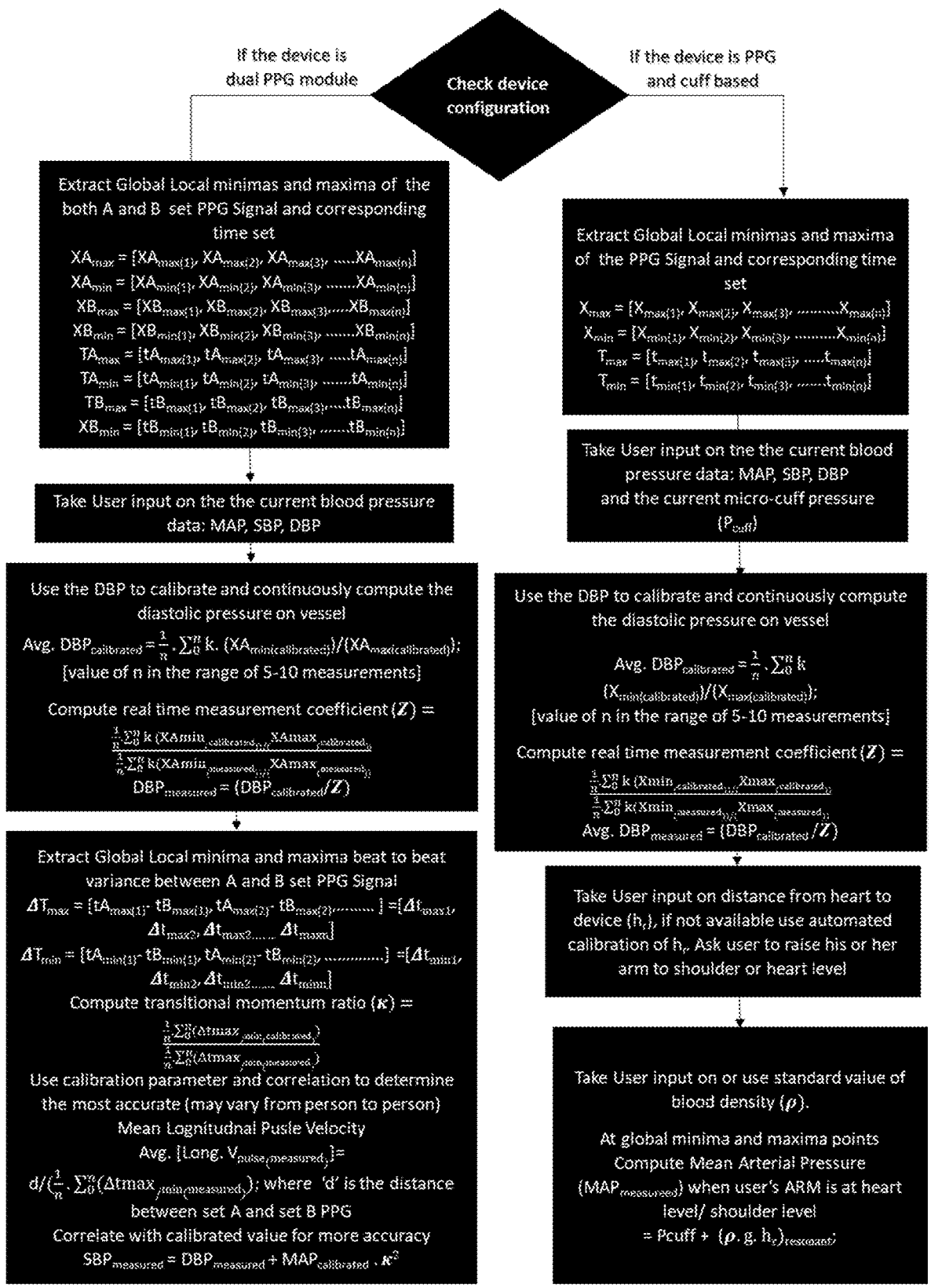

FIG. 3F describes the flow-diagram to compute real-time blood pressure levels from the real-time bio-signals. The extremum dataset (i.e. maxima and minima) of the real-time optical bio-signal response of the biosensors set and the user's input of blood pressure values in real-time with respect to time are recorded. A plurality of ratios between optical intensity ratio between the extremum (i.e. of maxima and minima) and that of user input of blood pressure values in real-time computed are analyzed and correlated to compute the real-time values of continuous blood pressure levels and diastolic pressure levels. In specific, a mean of summation of the plurality of ratios between the real-time extremum is correlated with user's input of blood pressure value to compute the blood pressure values. The dual sensor configuration is utilized to estimate momentum loss in the blood vessel during the change of the peaking of the blood pressure cycle to compute mean pressure and the systolic pressure levels. The momentum is inferred from the mean longitudinal pulse velocity (Avg. [Long. $V_{pulse}$(measured)]), which is computed based on ratio between the distance of the dual sensor (d) and on the time intervals between the extremum (either maxima or minima i.e. Δtmax/min) of the of real-time bio-signals of the dual sensors. In specific, the distance of the dual sensor (d) and the mean of the plurality ratios of the time intervals between the extremum (either maxima or minima i.e. Δtmax/min) of the real-time bio-signals of the dual sensors is computed to compute the mean longitudinal pulse velocity Avg. [Long. $V_{pulse}$(measured)]. The computed real-time blood pressure values from the ratios between the extremum, mean longitudinal pulse velocity and the user's real-time inputs of MAP, SBP, DBP are correlated to compute real-time blood pressure values of MAP, DBP from the bio-signals of the biosensors set. Whereas, heart to device reference length is used in the cuff based apparatus to measure the mean arterial pressure (as an alternative to manual user inputs).

Figure 3G:
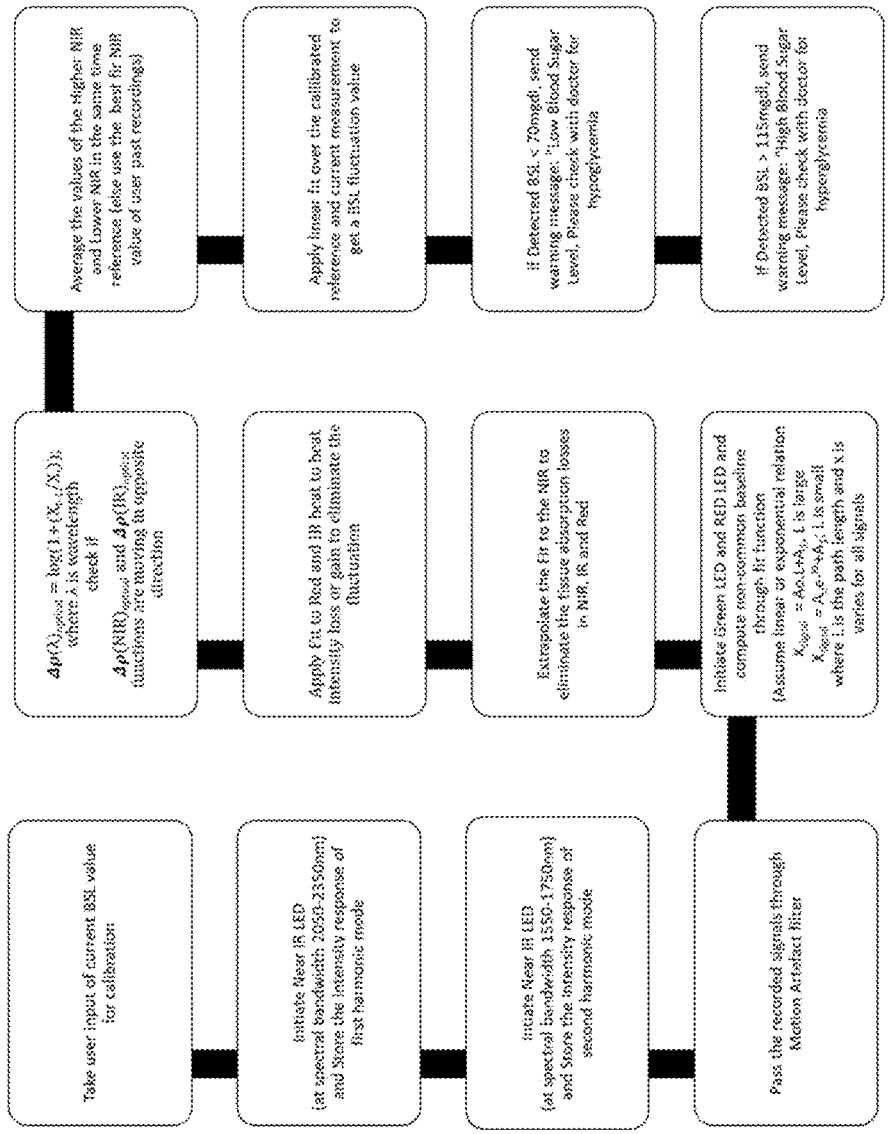

FIG. 3G describes the flow diagram to compute real-time blood sugar levels from the biosensors set. The real-time bio-signals of the green LED response, the red LED response, the infrared LED response and the near infrared LED response are correlated with real-time accelerometer signals (as described in FIG. 3A and FIG. 3B) to remove movement errors in the real-time bio-signals. The real-time bio-signals of the green LED response, the red LED response and the infrared LED response signals are correlated to the near infrared LED response signals to eliminate the blood flow fluctuations, tissue absorption, coherent errors and beat to beat fluctuations in the near infrared LED response signals to compute processed real-time near infrared response values. The current user inputs of blood sugar values in real-time and processed real-time near infrared response values are correlated to compute real-time blood sugar levels. The computed real-time blood sugar levels are analyzed for threshold value ranges to detect and compute hyperglycemia and hypoglycemia conditions.

Figure 3H:
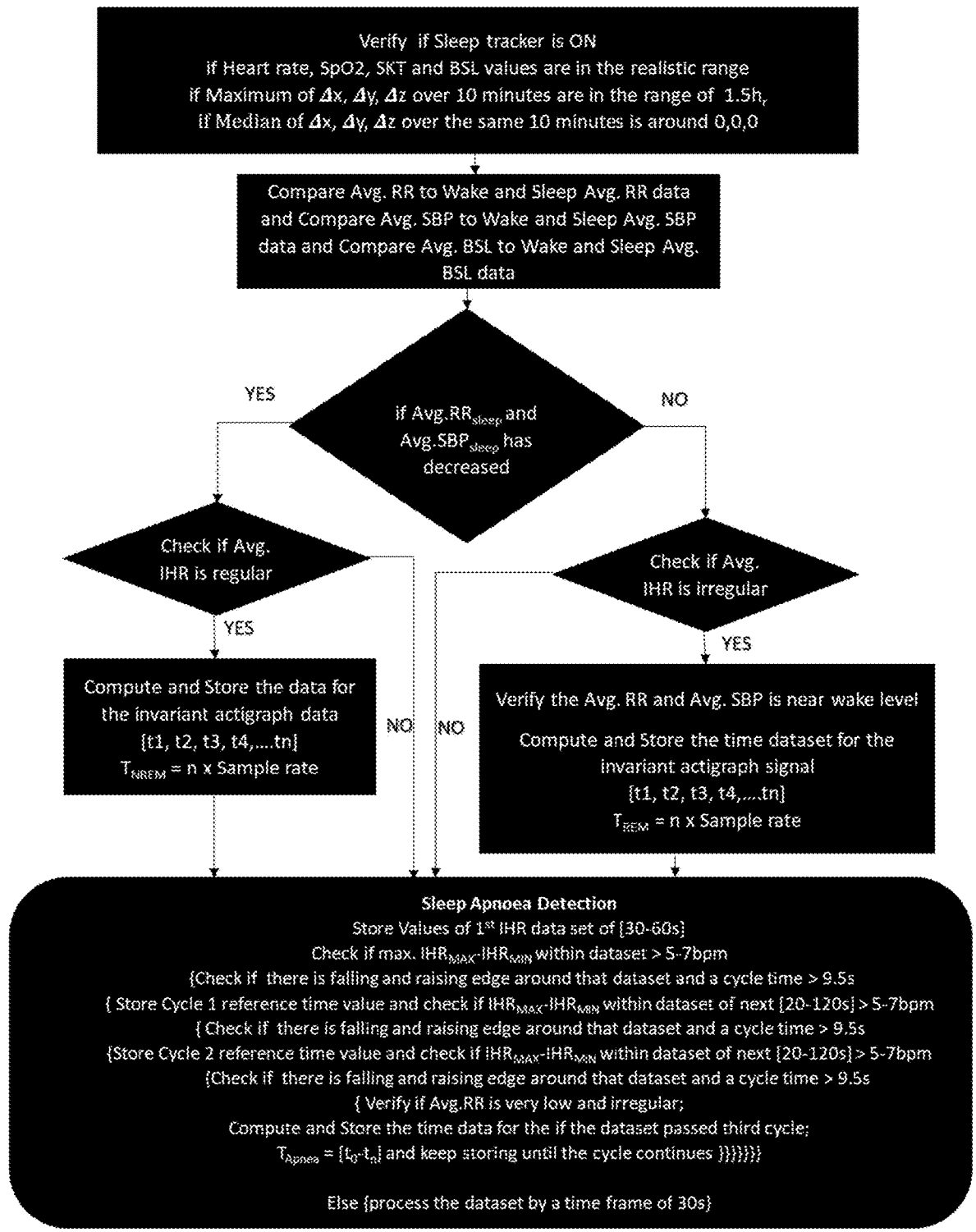

FIG. 3H describes flow-diagram to recognize and record sleep, various stage of sleep cycles and sleep apnea conditions from the real-time bio-signals of the biosensors set. The accelerometer signal values and realistic range of the real-time values of the heart rate, the oxygen saturation, the temperature response and the blood sugar levels are assessed to recognize that the user is in dormant or sleeping position. The computed real-time blood pressure levels and respiratory rate pattern are compared to the wake, activity or sleep pattern data to recognize the state of sleep and rest. The real-time blood pressure levels, respiratory rate pattern and instantaneous heart rate signals are further analyzed to track and compute the time periods of non-rapid eye movement sleep cycles and rapid eye movement sleep cycles. The real-time instantaneous heart rate dataset are analyzed in a time interval of 30-60 seconds and for 5-7 BPM difference window between the extremum of the dataset for falling and raising edges within a time window of 9.5 seconds, and further in a time interval of 20-120 seconds to recognize sleep apnea condition. The respiratory pattern within the recognized sleep apnea condition is further verified for low and irregular pattern to validate the sleep apnea condition. On recognizing the sleep apnea conditions, the time intervals of the sleep apnea are stored. Other suitable time frames, BPM difference windows, time windows and raising and falling edge forms of the exemplified form may be used to recognize sleep apnea condition. On recognizing mild to severe conditions of sleep apnea, a warning message is sent to the user and the life-support network.

Figure 3I:
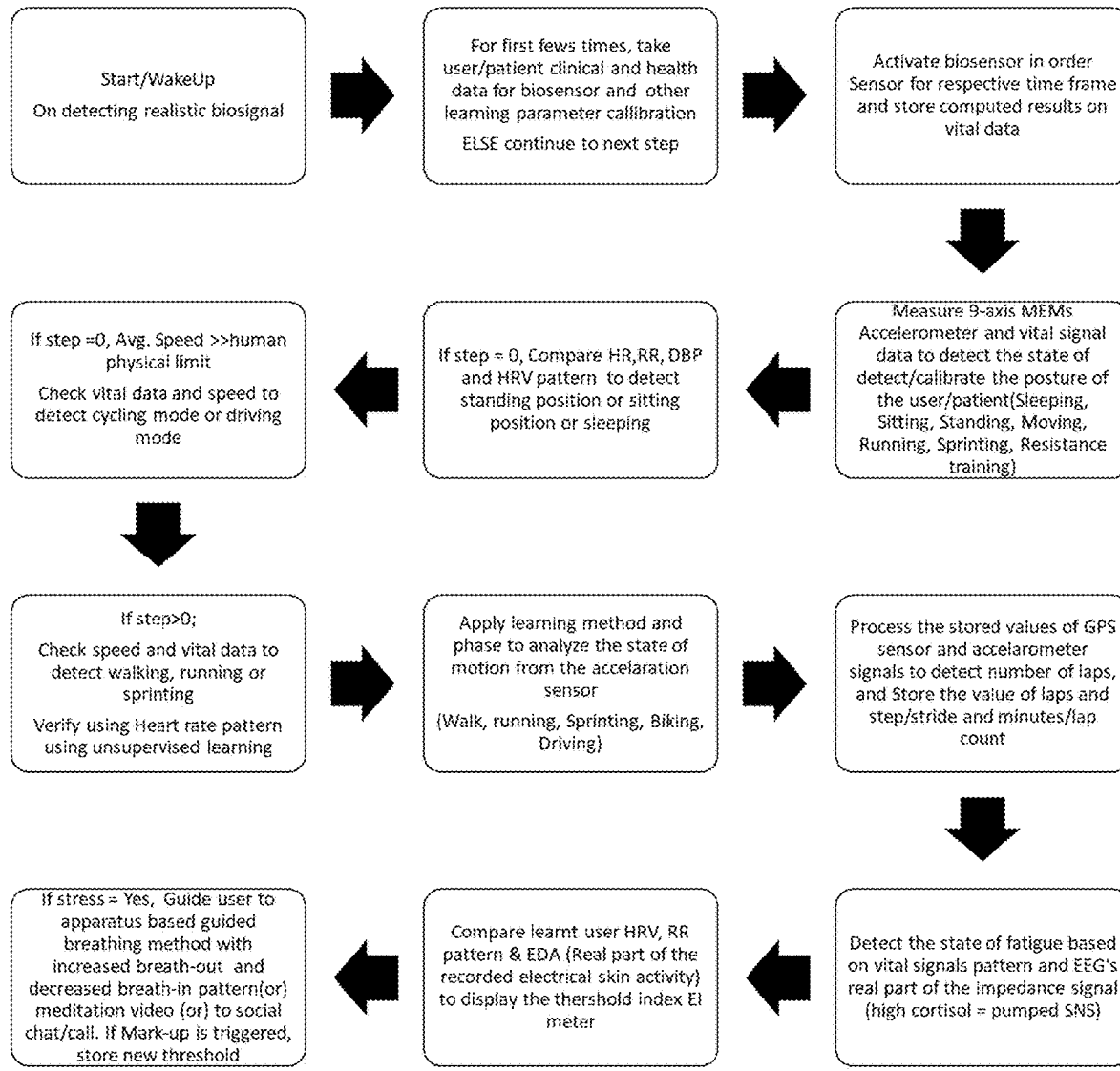
Figure 3J:
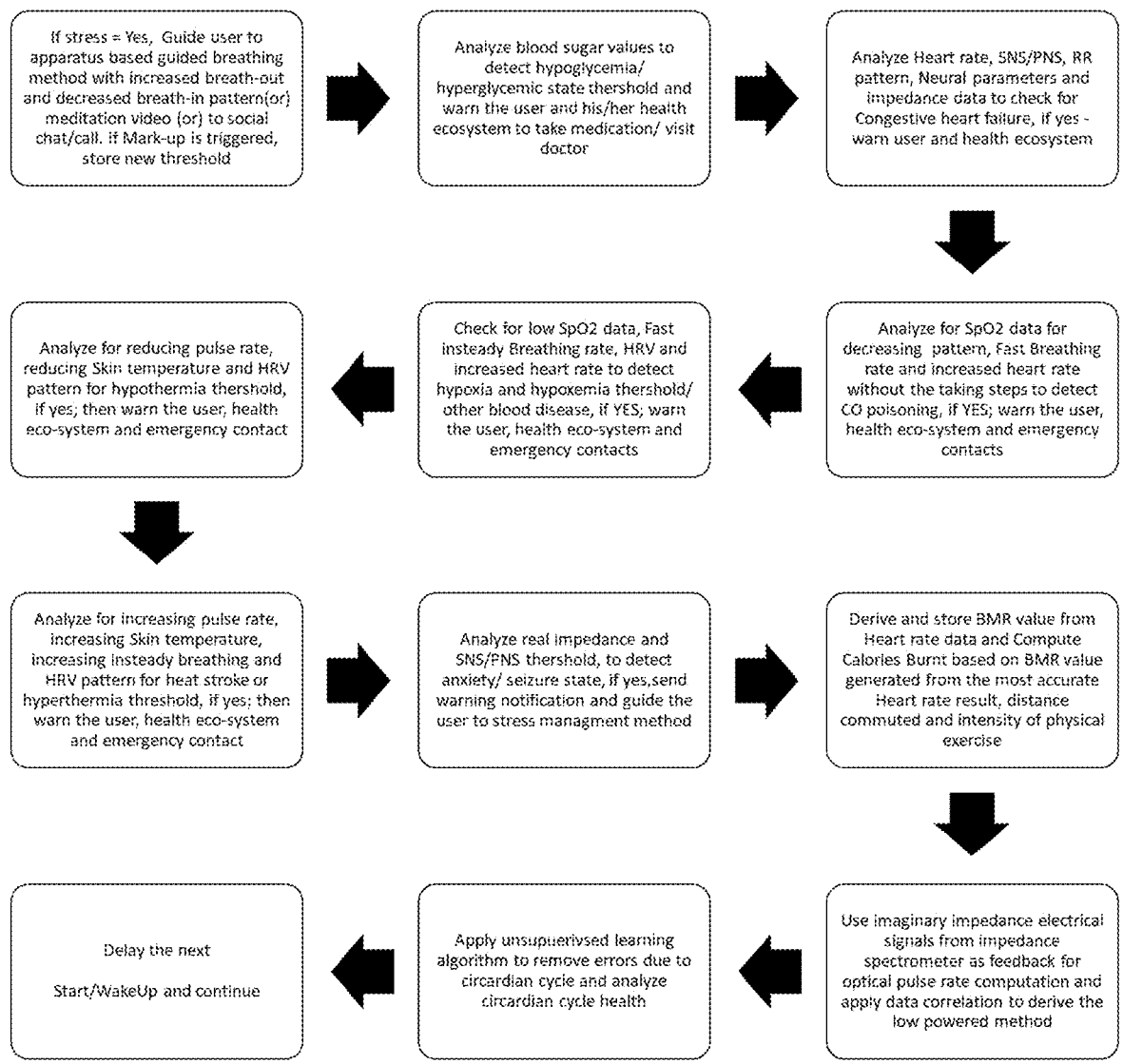

FIG. 3I and FIG. 3J describes flow-diagram to compute plurality of movement data, health conditions and clinical emergencies from the real-time bio-signals of the biosensors set and real-time accelerometer signals. The recorded real-time biological information, accelerometer values and user calibration values are analyzed by the emergency support apparatus to recognize plurality of movement data and clinical emergency conditions. On detecting realistic real-time bio-signals from the biosensors set, the emergency support apparatus is started or sent to wake mode. For first few times, inputs on the clinical data, health data and learning parameters from user are recorded for calibration. The real-time biological information of heart rate pattern, respiratory pattern, blood pressure pattern, blood glucose pattern, temperature, autonomous neural activity coefficients and parameters i.e. the vital signal data and the 9-axis accelerometer signals are analyzed to calibrate and detect the movement data of sleeping, sitting, standing, moving, running, sprinting and resistance training. The real-time heart rate pattern, pulse rate variability pattern, respiratory pattern and blood pressure patterns are analyzed at null steps or movement recognized from accelerometer signals to detect movement data of sleeping, sitting and standing. As described in FIG. 3B, the step movements can be detected from accelerometer or other suitable processing can also detect step movements. At null step movement or steps recognized from the accelerometer signals, the average speed of the emergency support apparatus extracted from the accelerometer signals is compared to human physical limit to compute movement data of cycling and driving. At recognized step movements, the speed of the emergency support apparatus extracted from the accelerometer signals at step movements and heart rate pattern are analyzed to compute movement data of walking, running or sprinting. Additionally, an unsupervised learning can be applied to the pulse rate variability or other real-time biological information and to the accelerometer signals to determine and compute the plurality of movement data comprising sleeping, sitting, standing, moving, running, sprinting, driving, biking and resistance training. The real-time vital signals pattern (i.e. real-time biological information) and the real-time real impedance response from the electrical biosensors set are analyzed to compute EI meter and to detect the fatigue condition and stress condition. The subjective stress levels thresholds are stored and detected from the user markups. The real-time blood sugar levels are analyzed to compute hypoglycemia condition and hyperglycemia condition. The real-time biological information and bio-signals of heart rate pattern, neural parameters (i.e. autonomous neural activity coefficients and parameters), respiratory pattern and impedance data (i.e. from AC signal response from electrical biosensors set) are analyzed to detect and compute congestive heart failure condition. A pattern of real-time biological information of decreasing SpO2 (oxygen saturation) pattern, fast respiratory rate pattern and increased heart rate pattern is analyzed to detect CO poising condition. A pattern of real-time biological information of low SpO2 (oxygen saturation) data, fast unsteady breathing rate pattern and decreasing heart rate pattern is analyzed to determine hypoxia, hypoxiemia and blood disease. A pattern of real-time biological information of reducing pulse rate pattern, reducing temperature and HRV (pulse rate variability) pattern are analyzed to determine and compute hypothermia condition. A pattern of real-time biological information of increasing pulse rate pattern, increasing temperature pattern, increasing unsteady breathing pattern and HRV (pulse rate variability) pattern are analyzed to recognize and compute hyperthermia condition. The real impedance response data from the electrical biosensors set is analyzed to recognize and compute the anxiety and seizure state. The response signals of electrical biosensors set and optical biosensors set are applied as feedback to rectify errors and accurately compute the plurality of real-time biological information, health conditions, movement data and clinical emergency conditions from the biosensors set. Further an unsupervised learning is applied to the vital signal data (i.e. real-time biological information) to remove errors due to circadian cycle and to compute the circadian cycle health. On recognizing any of the life-threatening emergency or clinical emergency conditions, the emergency support apparatus alerts the life support network.

As previously described, the computation and storage required in the series of flow-diagrams FIG. 3A to FIG. 3J can take place quickly and efficiently through a distributed combination of internal microprocessor of the emergency, the central server and network of accessorial devices (that includes accessorial mobile devices used by the user and life-support network i.e. plurality of devices operated by the life-support network).

Figure 4A:
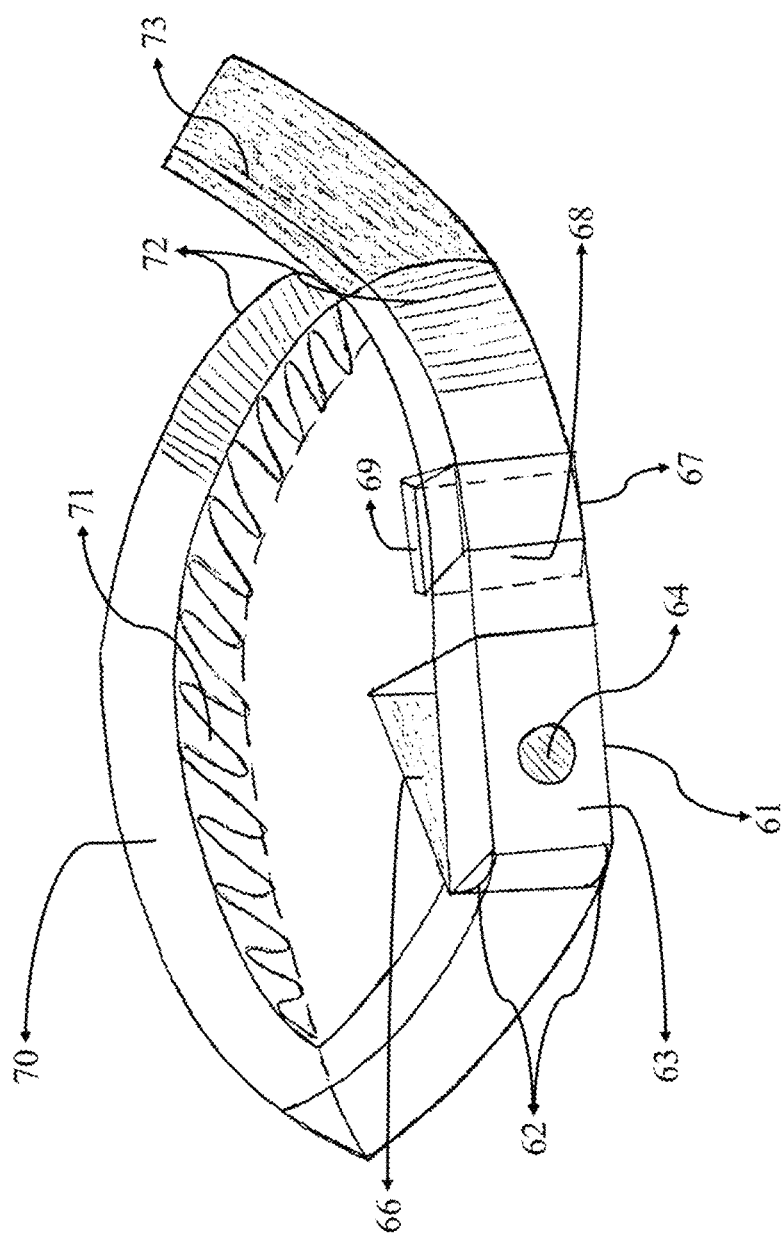
FIG. 4A is an isometric view of the child tracking apparatus embodiment form of the emergency support apparatus with magnetic buckle and pressure sensor.

FIG. 4A shows 3D-view of the child tracking device embodiment form of the emergency support apparatus. The child tracking (anti-abduction) apparatus has a belt buckle 61 with inbuilt pressure sensor 64, which keeps track of the pressure on the device through the victimizer or in any emergency event. The lower magnetic buckle element 66 and upper magnetically attractable buckle element 63 with an inbuilt pressure sensor 64 are held together through a spring-like hinge 62. The reflective sensing hardware 67, comprising of a detachable heat regulating case with bio-sensors 69 and a belt hole 68, is attached to the belt 70 through the belt hole element 68. The contact surface of the heat regulating case 69 is embedded with the plurality of biosensor probes (i.e. of the biosensors set) on the contact surface for extracting real-time biological and health data. The case 69 also contains the other essential hardware components. The buckle action and magnetic action created by the buckle 61 comprising of 63-62-66 is utilized for fastening to the belt. The belt 70 is made of up of cloth with inner foam base/sponge-like material 71 to avoid motion errors. The adhesion between the stickable surface pad 73 and adhesive surface pad 72 is also used to fasten the device to the user. The real-time biological information extracted by 3-4-5-6-7-8-9 (i.e. 25-26-27-28-29-30-31-32-33-34-35-36-37 in preferred biosensing hardware architecture), pressure data extracted by the pressure sensor set 2, movement data extracted by accelerometer 3 (i.e. 38 in preferred biosensing hardware architecture) and location data and movement data extracted by 10-11-12-13 are utilized for inferring the present condition of the user. These extracted real-time information (i.e the plurality of tracking information including the plurality of real-time biological information and clinical emergency condition, the plurality of movement data and pressure sensor set data such as real-time pressure data, abduction range, force and method of unbuckling indicating a event where the emergency support apparatus in unbuckled by the victimizer) is sent to synchronized accessorial devices, primary network device and other network of life-support devices.

Figure 4B:
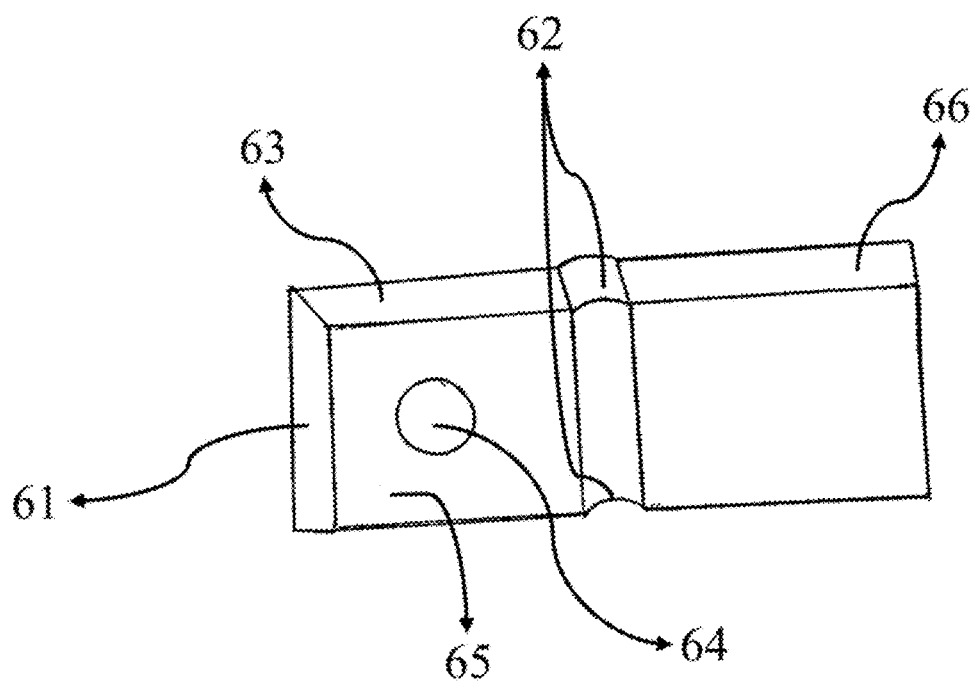
FIG. 4B is an isometric view of the magnetic buckle of the child tracking apparatus embodiment form.

FIG. 4B shows the magnetic buckle 61 of the child tracking device embodiment form. The pressure sensor 64 is embedded on the inner surface 65 of the magnetically attractable buckle element 63. The clamp 62, made up of spring like hinge material, holds the upper buckle element 63 and lower magnetic buckle element 66.

Figure 4C:
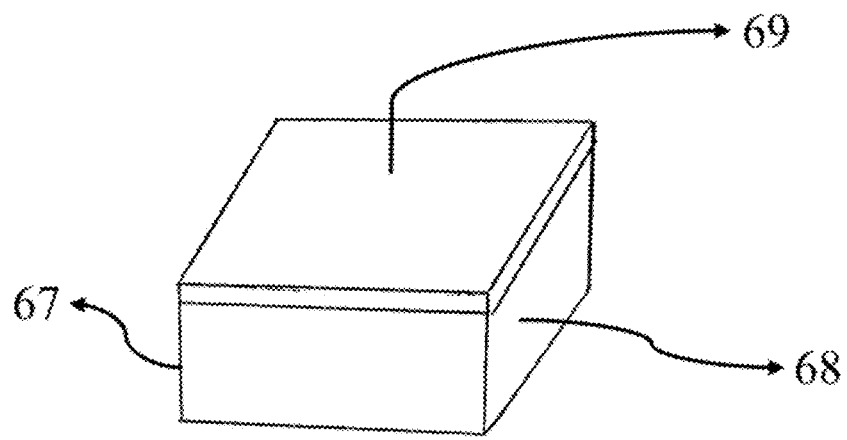
FIG. 4C is the reflective sensing hardware of the child tracking apparatus embodiment form.

FIG. 4C shows the reflective sensing hardware 67 of the child tracking apparatus. The plurality of bio-sensing probes (of the biosensors set) are placed on the contact surface of the detachable heat regulating casing 69. The reflective apparatus 67 has a hollow belt hole 68, which is used for attaching the device 67 to the belt 70. The hollow hole 68 is affixed below the case with sensors and electronics 69.

Figure 5:
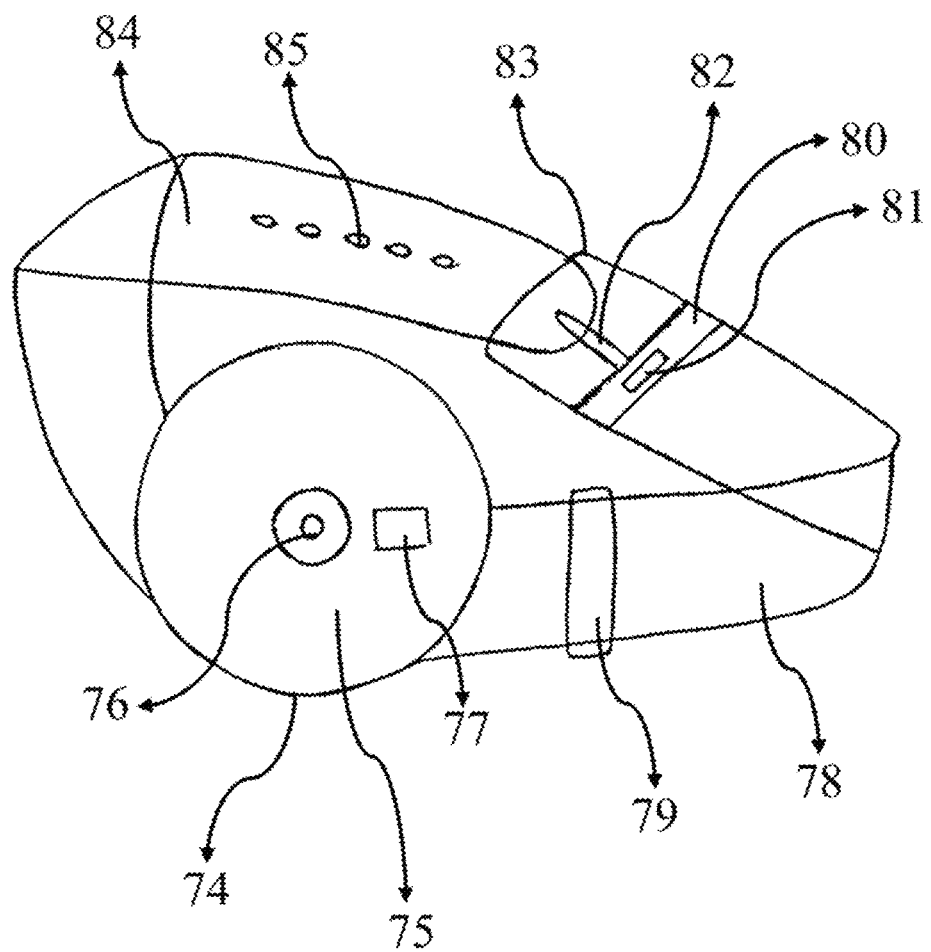
FIG. 5 is a smart wearable embodiment form of the emergency support apparatus with a novel strap technology.

FIG. 5 shows wearable emergency support apparatus embodiment form with a round structure near the contact surface. The device works the same way as described in the drawing FIG. 2. The rounded casing structure 74 on the contact surface 75 is used as means to evade cuts and injuries, that may otherwise occur due to the sharp edges. The pressure sensor 77 of the apparatus records the pressure data. The plurality of biosensors 76 embedded on the contact surface 75 of the frame 74 is utilized to record biological and health data (i.e. the plurality of real-time biological information and clinical emergency conditions). An additional pressure sensor 81 is affixed on the detachable buckle frame 80 of the front strap 78 for tracking the pressure data during the events of aggressively unstrapping the device or during other emergency events. The apparatus is fastened by attaching the buckle tongue 82 of the buckle 83 and free-loop 79 of the strap 78, to the back strap 84 with adjustment holes 85.

Figure 6:
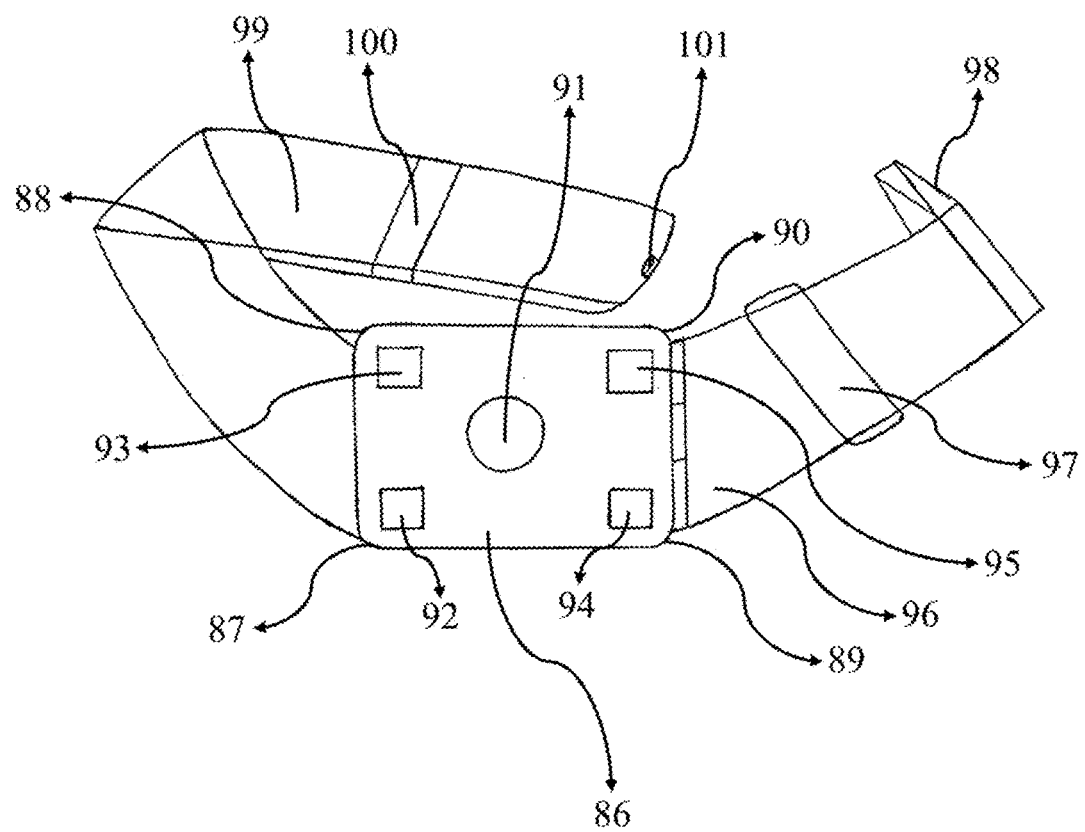
FIG. 6 is a four-pressure sensor configuration based smart wearable embodiment form of the emergency support apparatus.

FIG. 6 shows a wearable emergency support apparatus embodiment form with a rounded corner near contact surface. The device works the same way as described in the drawing FIG. 2. Instead, this apparatus has 4 pressure sensor configurations 92, 93, 94, 95 which are placed on the four corners of the smart wearable frame 86 to track the pressure data. The four pressure sensors 92, 93, 94 and 95 are used so that the pressure on the user can be accurately extracted over a single central pressure sensor. The 4 pressure sensors of 92, 93, 94 and 95 precisely tracks information on the direction of removal, force of removal and other parameters. The set of biosensors set and other sensors 91 is placed on the contact surface of the device frame 86, which is used to extract the biological data, health data and other important information (i.e. the plurality of real-time biological information and clinical emergency conditions). The rounded corners 87-88-89-90 of the device frame 86 is utilized to evade cuts and injuries. The emergency support apparatus is fastened through straps 96-99 with free loop 97 and magnetic buckle 98-100. The apparatus has a free-loop 97 and a fixed magnetic attractable buckle element 98 on the front strap 96, and it has a movable magnetic clasp 100 on the back strap 99. The device is fastened on the wrist or other body parts by inserting the strap 99 through buckle element 98 and free-loop 97 until the movable magnetic clasp/bar 100 is magnetically attracted by the element 98. The movable magnetic element 100 is locked through a stopper 101 affixed on the strap 99, and the solid stopper 101 inhibits the freely movable clasp 100 from slipping out of the strap 99.

Figure 7:
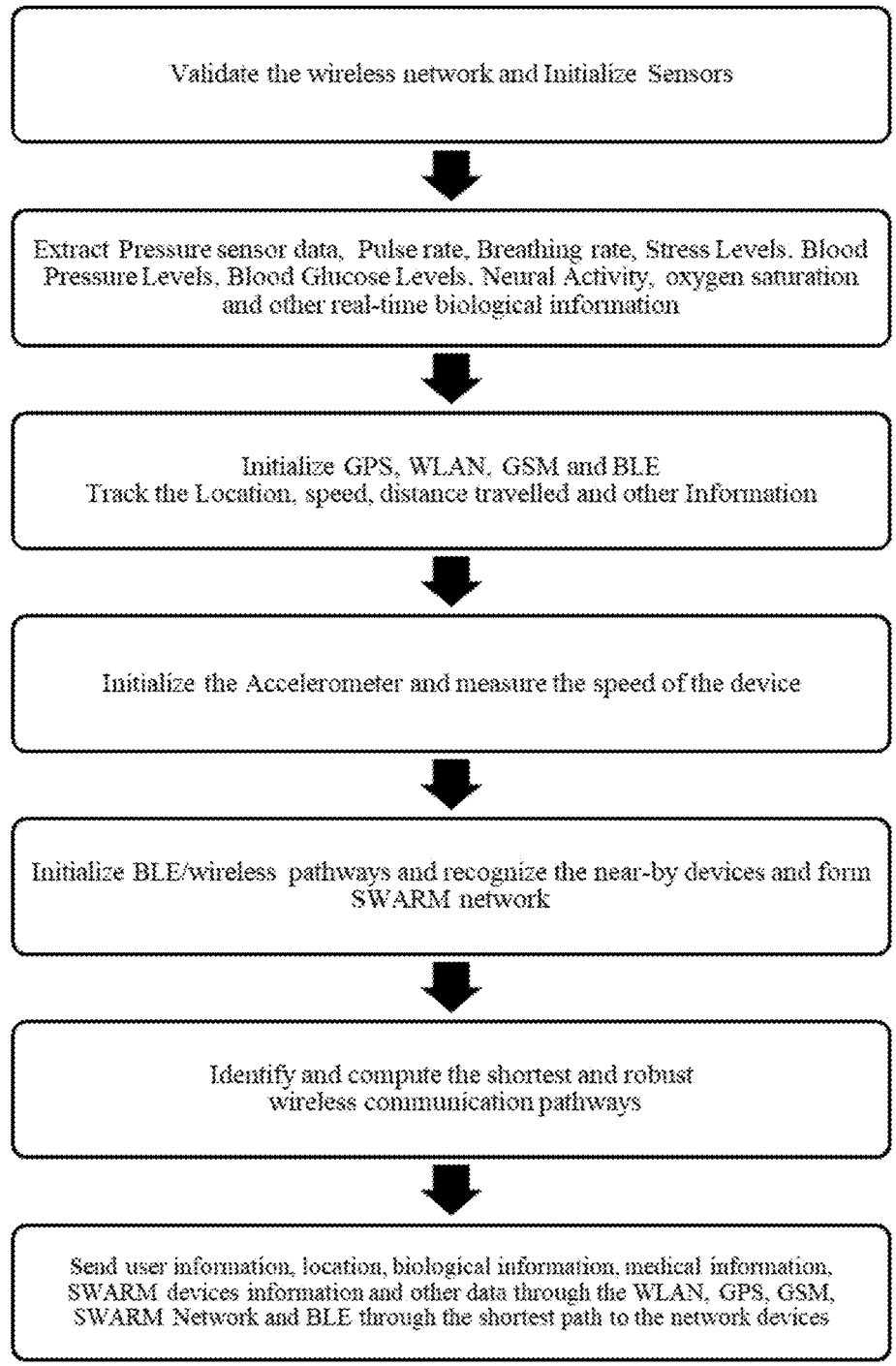
FIG. 7 describes the flowchart for extracting and communicating the real-time tracking information.

FIG. 7 shows the flow-chart for extracting and communicating real-time tracking information. Initially, the wireless network of the emergency support apparatus is validated, and the sensors (i.e. pressure sensor set, biosensors set and accelerometer) and wireless antennae of the emergency support apparatus are initialized. The real-time pressure sensor data (of real-time pressure, force and method of unstrapping, direction of removal and whether aggressively unstrapped as result of victimizer) and the plurality of real-time biological information and clinical emergency conditions are computed and recorded. The wireless antennae set of GPS, GSM, Bluetooth and WLAN are initialized and the emergency support apparatus's location, speed, distance travelled and other information are recorded. The accelerometer of the emergency support apparatus is initialized to track and record the plurality of movement data, the speed and the distance travelled. The emergency support apparatus forms the SWARM smart devices network through the Bluetooth/wireless network and records the information about the SWARM devices. Then, the shortest and most robust communication pathway is identified. The recorded information is sent through the shortest communication path of the WLAN, GPS, GSM, SWARM Network and BLE to the life-support network, client devices, SOS network and other near-by devices (i.e. in the location vicinity of the emergency support apparatus).

Figure 8:
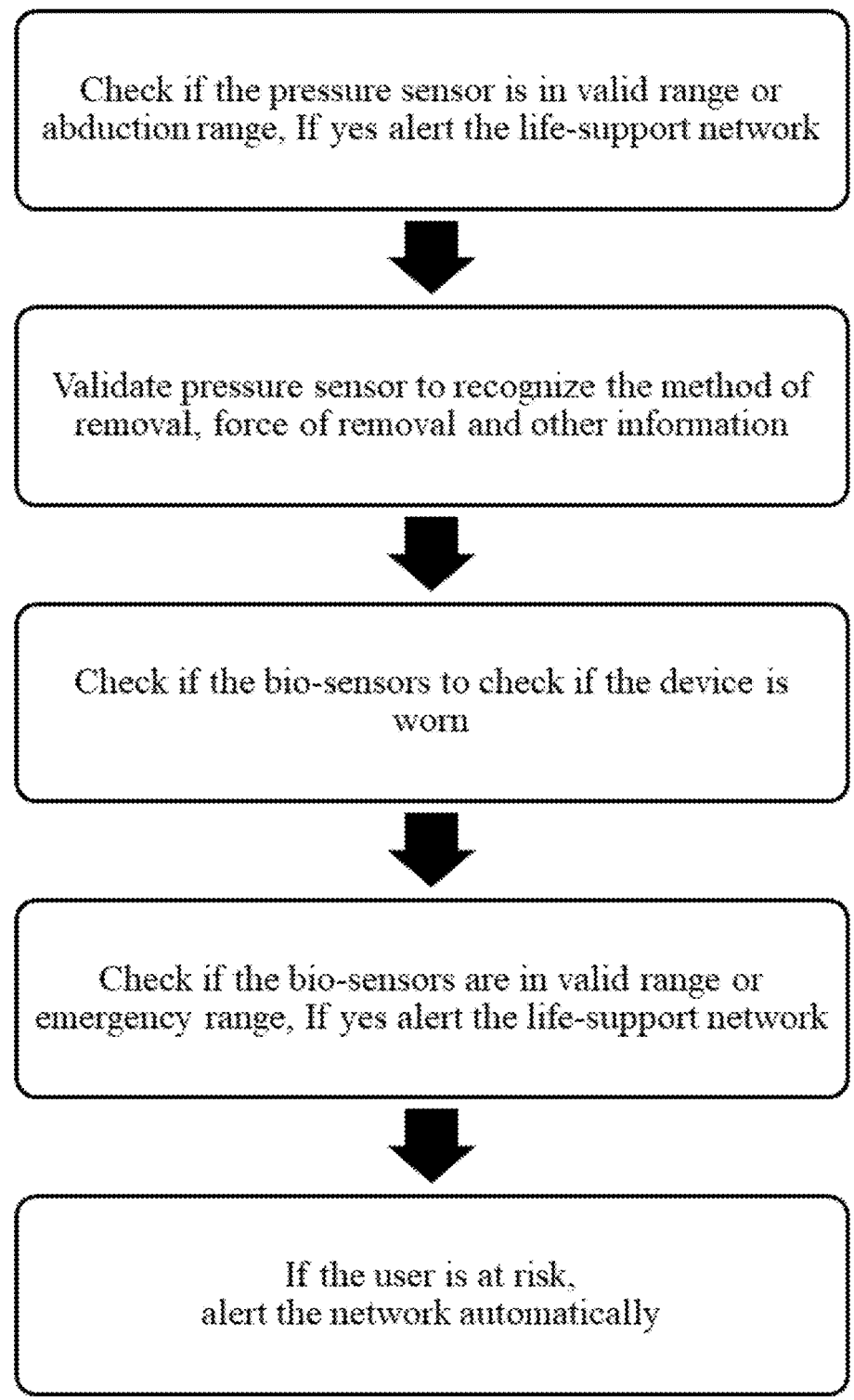
FIG. 8 describes the basic flow-diagram for automatically activating trigger commands.

FIG. 8 describes the flow-diagram for automatically activating trigger commands in the life-support network. Initially, the pressure sensor set is analyzed for valid pressure range or abduction range, the method of removal, device status, force of removal, direction of removal and other information. The pressure sensor set placed in suitable spots as in befit embodiments as described in FIG. 4, FIG. 5 and FIG. 6 can indicate whether it is victimizer method of emergency support apparatus removal. The biosensors set are analyzed to validate if the user is wearing the device. The plurality of real-time biological information and clinical emergency conditions from the biosensors set are validated to recognize emergency condition. The tracking information tracked from the biosensors set or the pressure sensor are analyzed for the emergency range (i.e. due recognized clinical emergency conditions, abduction range or an event indicating the victimizer method of unstrapping, etc). The life-support network is automatically alerted, once the user at risk is confirmed due emergencies (like abduction, clinical emergency or any other emergency). The user at risk is confirmed if the tracking information tracked from the biosensors set or the pressure sensor are in the emergency range (i.e. due recognized clinical emergency conditions, abduction range or an event indicating the victimizer method of unstrapping, etc).

Figure 9:
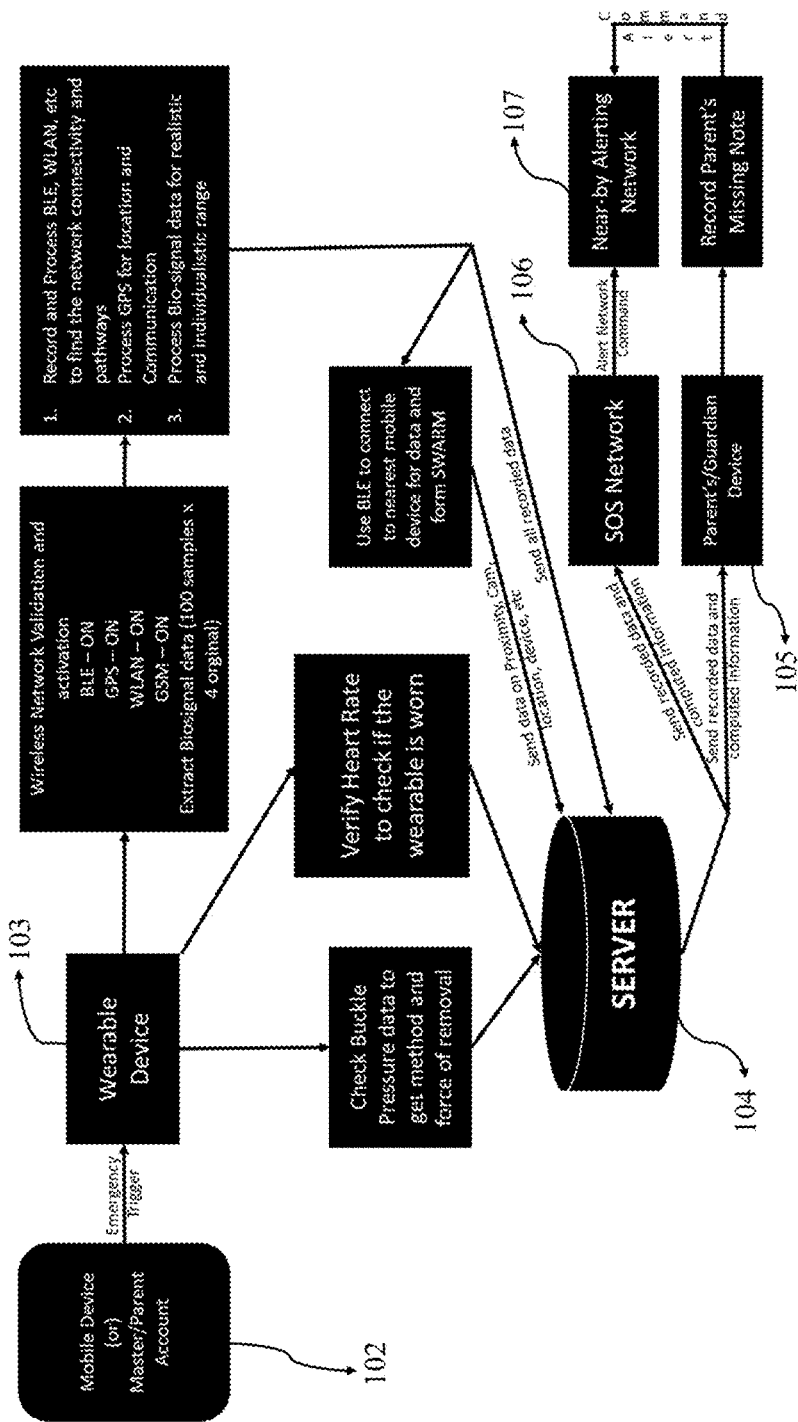
FIG. 9 describes the flow-diagram when trigger commands are triggered.

FIG. 9 shows the flow-diagram of the course of action on activation of trigger commands either due to the trigger of trigger commands by the life-support through their devices or due to automatic recognition of user at risk that is obtained from the real-time data of pressure sensor and biosensors set. As soon as the "emergency" command is triggered by the emergency support apparatus 103 or master/client device 102, the emergency support apparatus 103 begins by validating the status of its internal Wireless Network connections (like GPS, GSM, WLAN, BLE) and it simultaneously "checks pressure sensor data". The current pressure sensor data on the mobile device 103 is utilized to sense the pressure on the user and method of device removal. The pressure sensor set in befit embodiment forms as described in FIG. 4, FIG. 5 and FIG. 6 can recognize whether the emergency support apparatus is unstrapped by a victimizer. The emergency support apparatus verifies biosensor set and pressure data to check status of the wearable (like if the device is worn and the user status). After network validation, the emergency support apparatus 103 assesses wireless modules for location data, movement data and communication pathways to the central server 104 and client network devices of parent/guardian device 105, SOS network 106 and near-by altering network devices -107 (i.e. in the location vicinity of the emergency support apparatus). The emergency support apparatus finds nearby Bluetooth/wireless devices and forms the SWARM network for new communication pathways. The emergency support apparatus 103 processes nearby wireless smart devices for communication and life-support network reference data. Then the plurality of recorded network data, tracking information, missing note, location data, bio-sensor data, pressure sensor data and other information is sent through WLAN, GPS, Bluetooth, SWARM Devices and GSM to the central server 104, SOS Network 106 and client devices (i.e. parent or guardian device) 105. Whenever the alert command is triggered by the 102, 103, 105 and 106, the real-time tracking information, missing note and notifications are sent to the near-by devices 107 in the emergency location (i.e. location of the emergency support apparatus). As previously described, the missing note for disclosing more particular information about the user is recorded by 103, 105 and/or 106. As previously described, the SWARM network is established through a plurality of intermediate wireless SWARM devices and the real-time tracking information is communicated through computed shorter and robust communication pathways that includes the SWARM network. As previously described regarding the plurality of real-time tracking information, the plurality of real-time tracking information includes the real-time pressure sensor set data (of real-time pressure, valid or abduction range, force of removal, method of removal, direction of removal, etc), the plurality of movement data obtained from the accelerometer, the plurality of location and movement data obtained from the wireless antenna set and the plurality of real-time biological information and clinical emergency conditions, the health conditions of the user, the device status to indicate whether the emergency support is worn by the user, etc. As previously described, the computation and storage can take place quickly and efficiently through a distributed combination of internal microprocessor of the emergency, the central server and network of accessorial devices (that includes accessorial mobile devices used by the user and life-support network i.e. plurality of devices operated by the life-support network).

Figure 10:
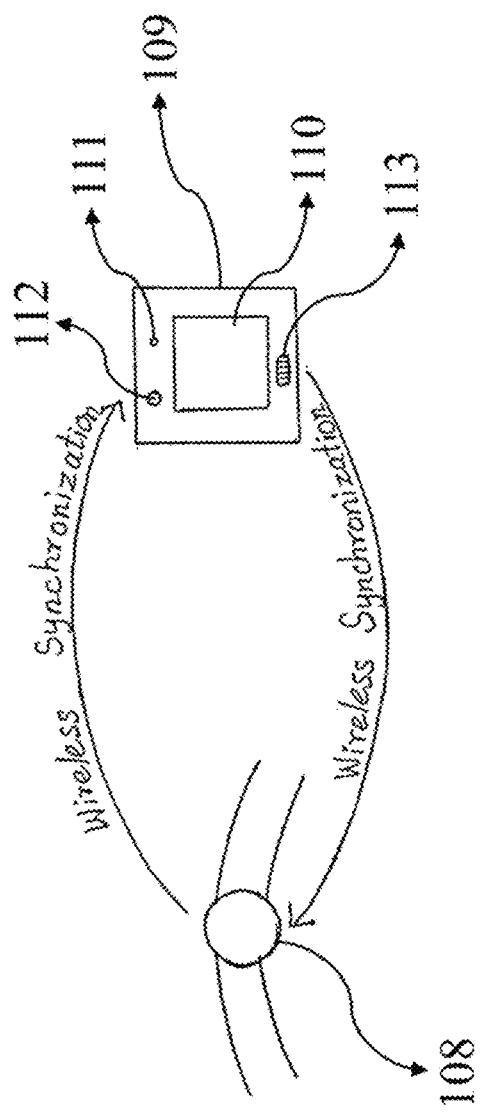
FIG. 10 shows an accessorial mobile device wirelessly synchronized with the emergency support apparatus.

FIG. 10 is an accessorial mobile device 109 that is wirelessly synchronized with the emergency support apparatus 108. The wireless emergency support device 108 is wirelessly connected and synchronized with the accessorial mobile apparatus 109. The trigger commands, emergency support apparatus 108 and its embodiment forms, and the in-built applications are operated through the accessorial device 109. The computed real-time tracking information and recorded data are viewed on the display 110 of the accessorial mobile apparatus 109. The accessorial mobile apparatus 109 communicates the real-time and recorded information to the life-support network. The touch display 110 of the accessorial mobile apparatus 109 is also utilized to operate the emergency support device 108, to trigger emergency/alert commands and to access the in-built applications. The video camera 112 and mic 111 of the acessorial mobile device 109 are used to perceive the events of emergency. Additionally, the video camera 112 and the mic 111 are also utilized to operate the emergency support apparatus and in-built applications. The speaker 113 of the accessorial mobile device 109 is utilized to perceive the life-support network's responses. The wireless emergency support apparatus 108 utilizes the accessorial mobile device 109 for computational and data storage purposes.

Figure 11A:
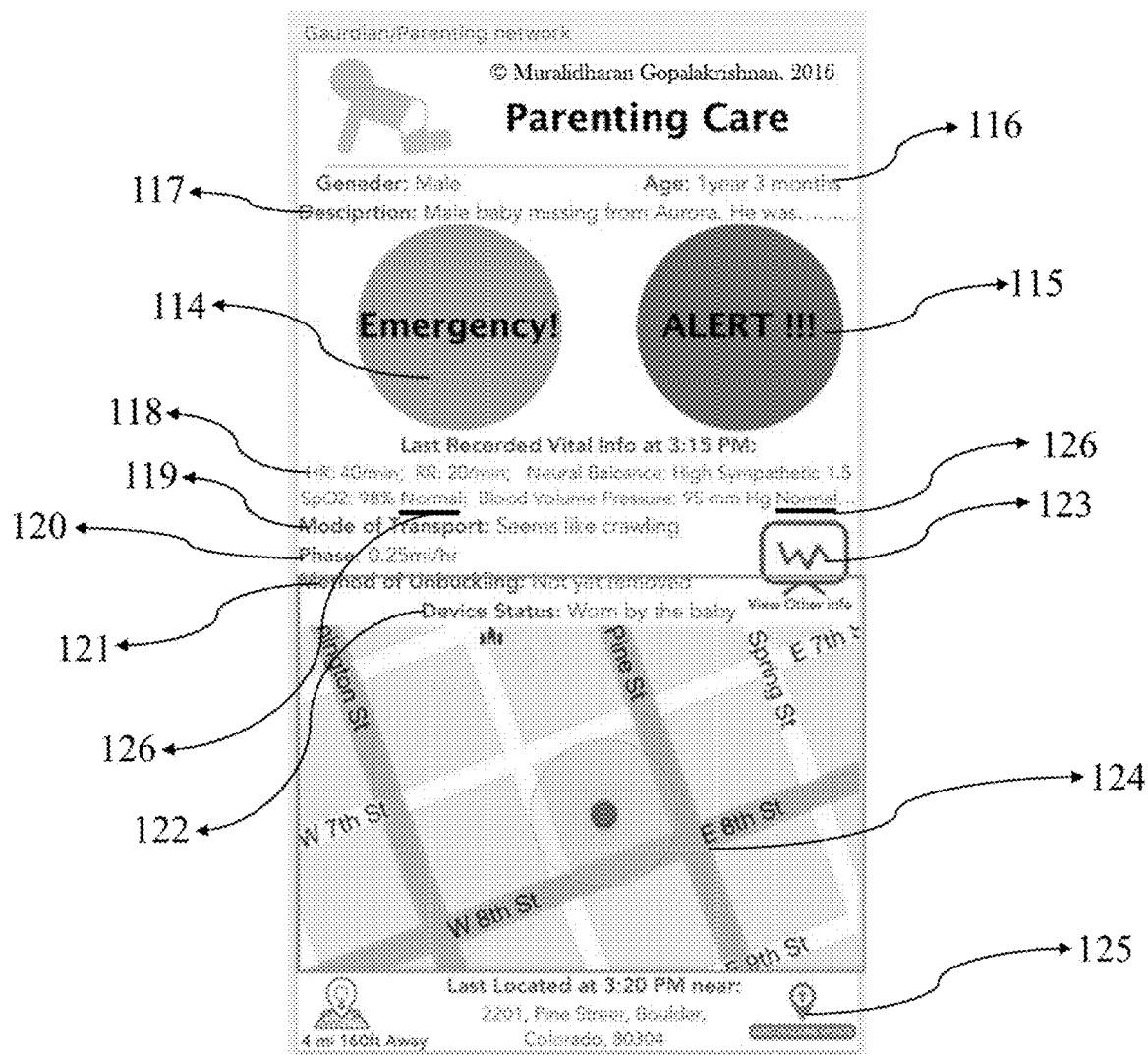
FIG. 11A and FIG. 11B show the child tracking software application.
Figure 11B:
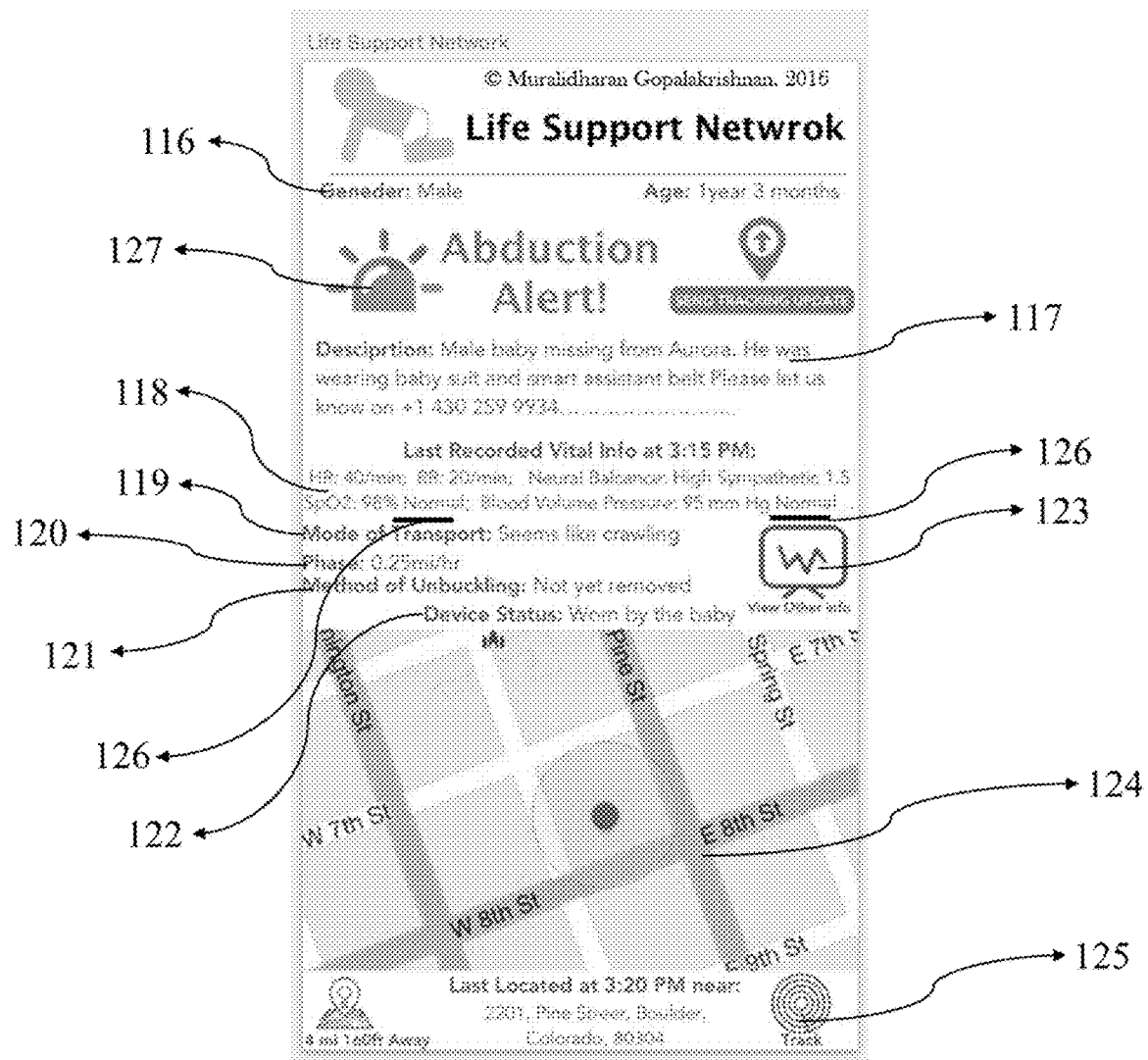

FIG. 11A and FIG. 11B is the accessorial application interfaces for child-tracking application. FIG. 11A shows the basic buttons of Emergency button 114 and Alert button 115 of the parenting care application of the mobile apparatus. The buttons 114 and 115 are triggered to activate emergency or alert command in the wireless life-support network. The emergency support apparatus's location 124, transportation mode 119, speed 120, current biological conditions 118 (i.e. real-time biological information of the user wearing the emergency support apparatus), method of unbuckling 121, device status 122 and user information 116 are displayed on the application. The trigger commands are activated either automatically based on the detected user condition, or through the triggering emergency/alert command in the accessorial user application. On pressing the emergency command 114, the apparatus instantly verifies and displays the real-time tracking information on the devices operated by the life-support network. On triggering the alert command 115, the tracking information are sent to the client devices (i.e. the life support network) and other network devices in the location of emergency (i.e. nearby device in the location of the emergency support apparatus). The track or send tracking update 125 of the parenting care apparatus updates and shares the location data with the life-support network. FIG. 11B shows the life-support application that appears on the triggering the Alert or the Emergency trigger buttons. Once the trigger command is recognized, the abduction alert 127, location data 124, transportation mode 119, speed of emergency support apparatus 120, current biological conditions 118 (i.e. real-time biological information of the user wearing the emergency support apparatus along with short description on real-time biological information 126), method of unbuckling 121, device status 122, user information 116, missing note 117 and other real-time tracking information are displayed on SOS Network 106, client devices 105 (i.e. parent or guardian device) and other nearby network devices 107. The track button 125 on the life-support network application is utilized to update and share the location data in the life-support network. The missing note 117 is recorded and sent by the primary network 102-103 or the SOS network 106. The primary parenting care application and life-support network application have a live vital monitor option 123, through which detailed live biological signals are monitored. The real-time biological information 118 comprises of short description 126 on the present medical condition and real-time data on pulse rate, breathing rate, oxygen saturation, neural activity, blood glucose levels, blood pressure data, stress levels and body temperature. As shown in the FIG. 11A and FIG. 11B, the short description on present medical condition or real-time biological information 126 indicates whether the plurality of the real-time biological information is normal or abnormal. The live vital monitor 123 to monitor detailed live biological signals i.e. signal forms of the real-time biological information can obtained through the real-time signal forms of the real-time bio-signals of biosensors set as described in series of FIG. 3, where flow-diagrams to compute individual biological information along with their bio-signals is described in series of FIG. 3. The applications as described in FIG. 11A and FIG. 11B can be operated by the life-support network or primary network through their mobile devices.

Figure 12A:
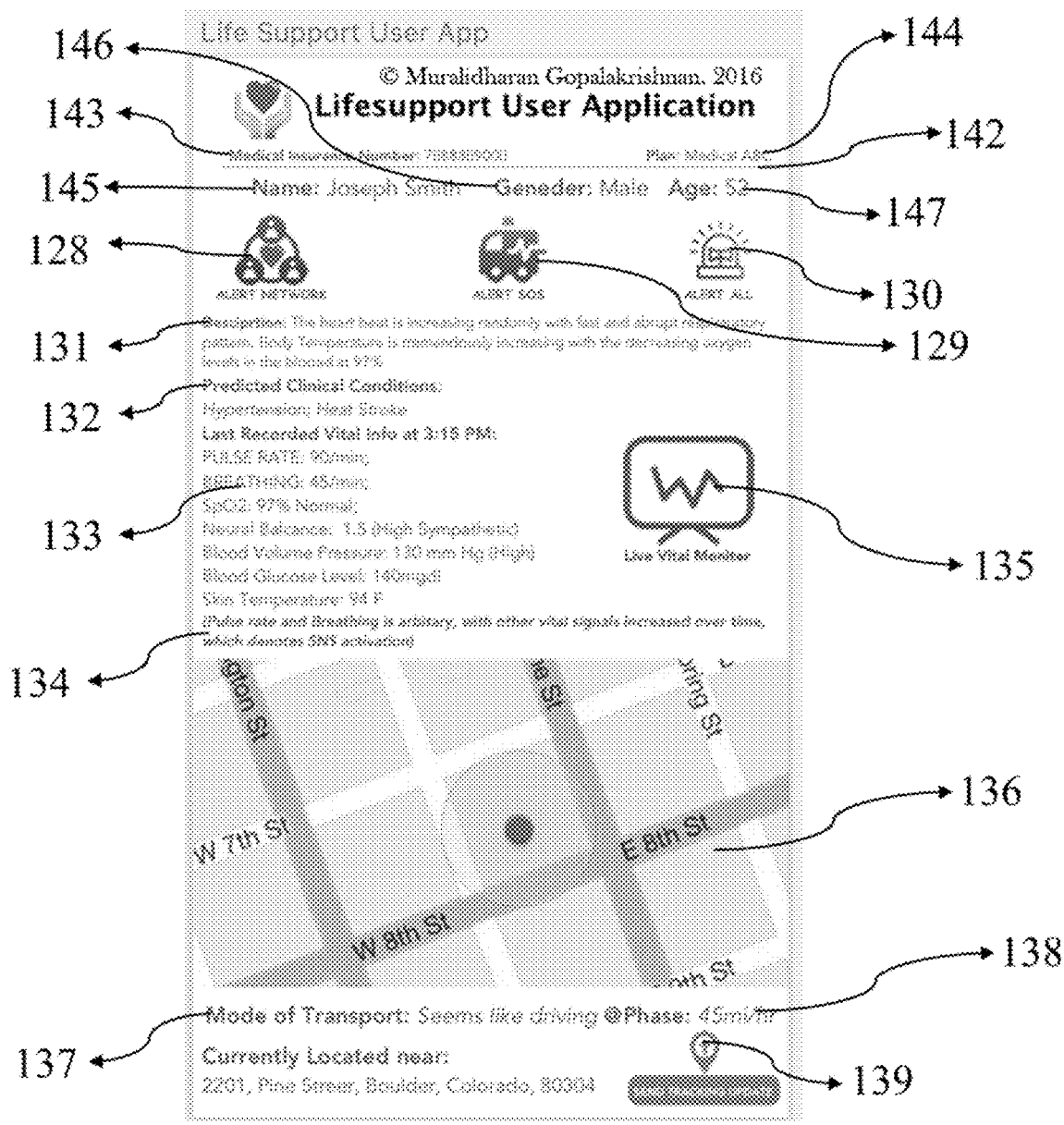
FIG. 12A and FIG. 12B show the user and client software interface of clinical emergency application.
Figure 12B:
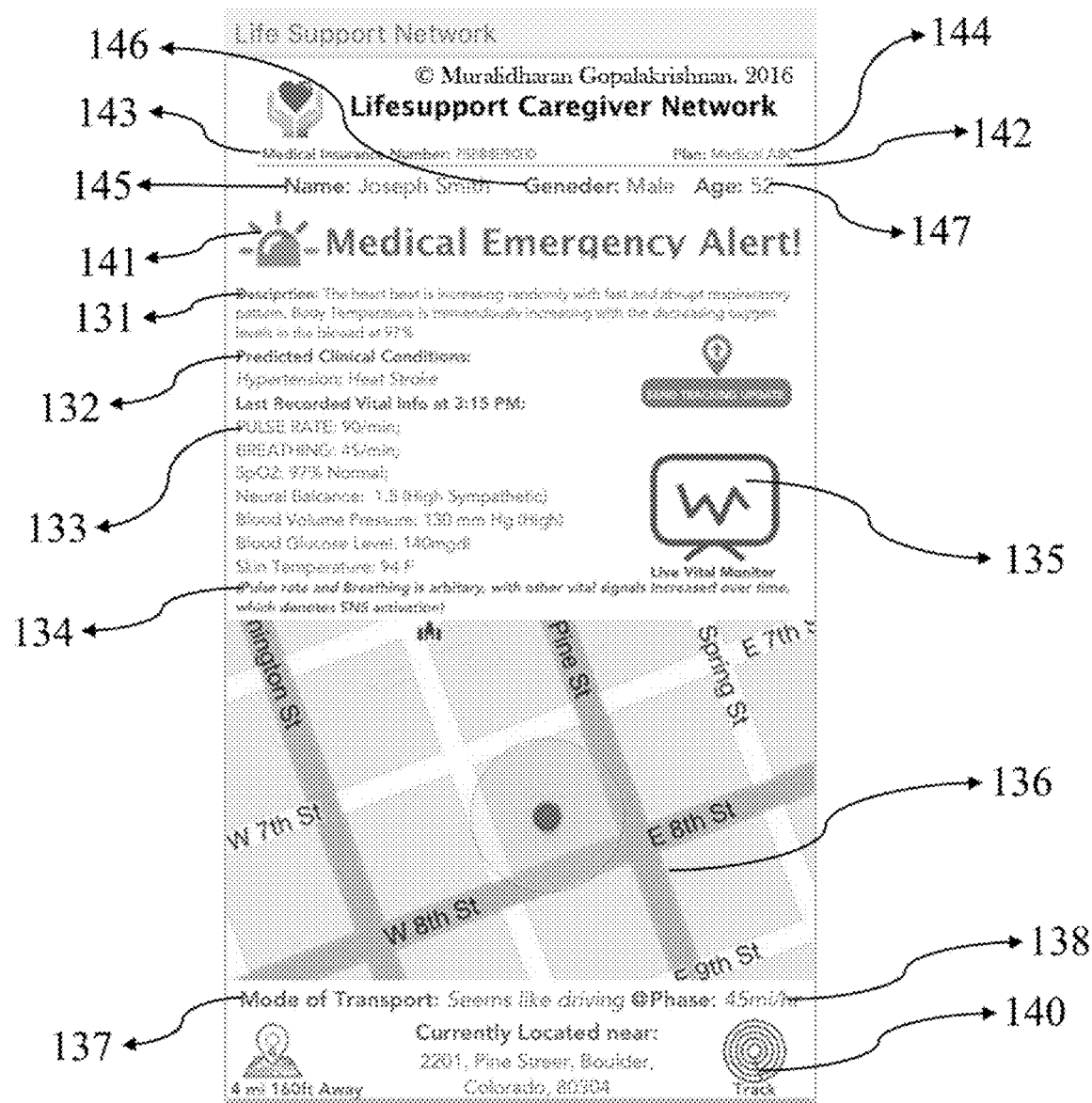

FIG. 12A and FIG. 12B is the user and client software interface for clinical emergency application. FIG. 12A is the software application that displays user information 142, automated medical condition description 131, predicted clinical condition 132, location data 136, mode of transportation 137, transportation speed 138, and real-time biological information 133. The user application has trigger buttons of Alert network 128, Alert SOS 129 and Alert All 130 for alerting the personal network, personal network, SOS network and other nearby network devices in the vicinity. The Alert Network trigger button 128 alerts the personal network (i.e. parent/guardian device and social network of the life-support network). The Alert SOS trigger button 128 alerts the SOS network. The Alert All trigger button 128 alerts the SOS network, the personal network and the nearby network devices in the vicinity of emergency support apparatus. The personal network includes social network and life-support network. The track or send tracking update option 139 on the user application updates and shares the location data with the life-support network. FIG. 12B is the client application interface when the emergency/alert command is triggered. The client or life-support application displays a medical alert 141, user information 142, automated medical condition description 131, predicted clinical condition 132, location data 136, mode of transportation 137, transportation speed 138, and real-time biological information 133. The live vital monitor 135 option in the user application and client application is utilized to view real-time signals. The user information 142 comprises of data on user name 145, age 147, gender 146, medical plan 144 and medical insurance number 143. The track or send tracking update option 139 on the client interface is used to update and share the location data in the life-support network. The real-time biological information 133 comprises of short description 134 on the present medical condition and real-time data on pulse rate, breathing rate, oxygen saturation, neural activity, blood glucose levels, blood pressure data, stress levels and body temperature. As shown in the FIG. 12A and FIG. 12B, the short description on present medical condition or real-time biological information 134 indicates whether the plurality of the real-time biological information is normal or abnormal. As shown in the FIG. 12A and FIG. 12B, predicted clinical condition 132 conveys the type of clinical emergency conditions (eg: hypertension, heat stroke as exemplified in FIG. 12A and FIG. 12B). As shown in the FIG. 12A and FIG.

12B, automated medical condition description 131 descriptively conveys the pattern of plurality of real-time biological information (example as exemplified in FIG. 12A and FIG. 12B: The heart beat is increasing randomly with fast and abrupt respiratory pattern. Body Temperature is tremendously increasing with decreasing oxygen levels). The live vital monitor 135 to monitor detailed live biological signals i.e. signal forms of the real-time biological information can obtained through the real-time signal forms of the real-time bio-signals of biosensors set as described in series of FIG. 3, where flow-diagrams to compute individual biological information along with their bio-signals is described in series of FIG. 3. The applications as described in FIG. 12A and FIG. 12B can be operated by the life-support network or primary network through their mobile devices.

FIG. 13 is an accessorial emergency support apparatus with video camera device, that is attached to the emergency support device, for video conferencing and secretively perceiving the emergency events.

Figure 13A:
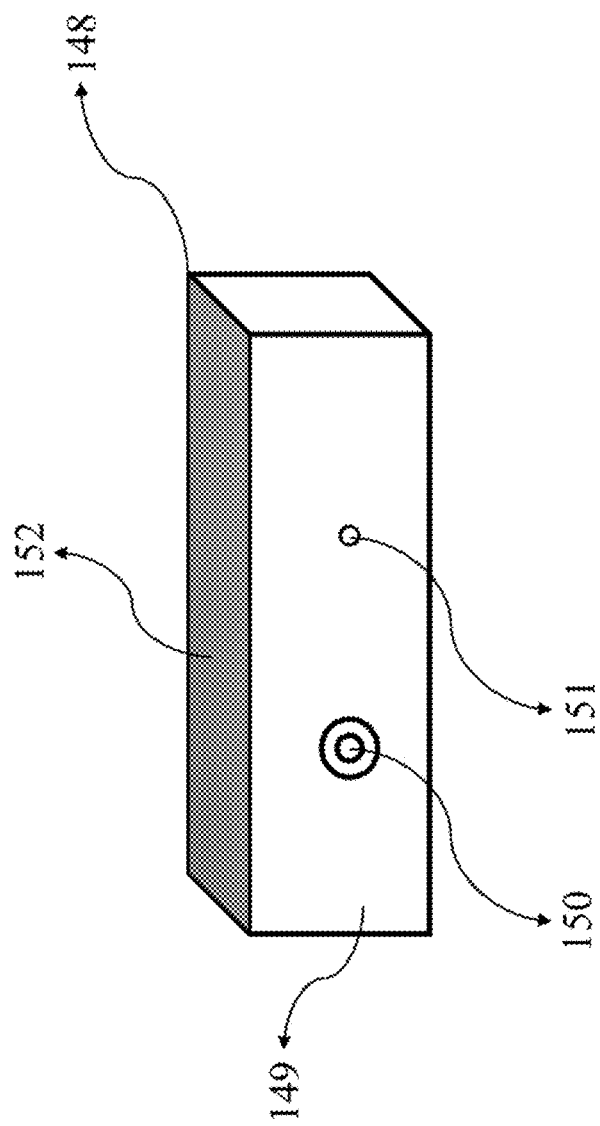
FIG. 13A shows a front isometric of the video camera based accessorial emergency support apparatus.

FIG. 13A is the front isometric view of the accessorial emergency support apparatus. The device 148 has high definition video camera 150 and microphone 151 on the front surface 149 that is used for secretively perceiving the events of emergency. The video camera 150 and microphone 151 are utilized to operate the device 148 and its in-built applications. It has a detachable and adhesive surface 152 on the top or bottom surface, that is utilized for attaching and mounting the 148 on the primary emergency support apparatus and other surfaces.

Figure 13B:
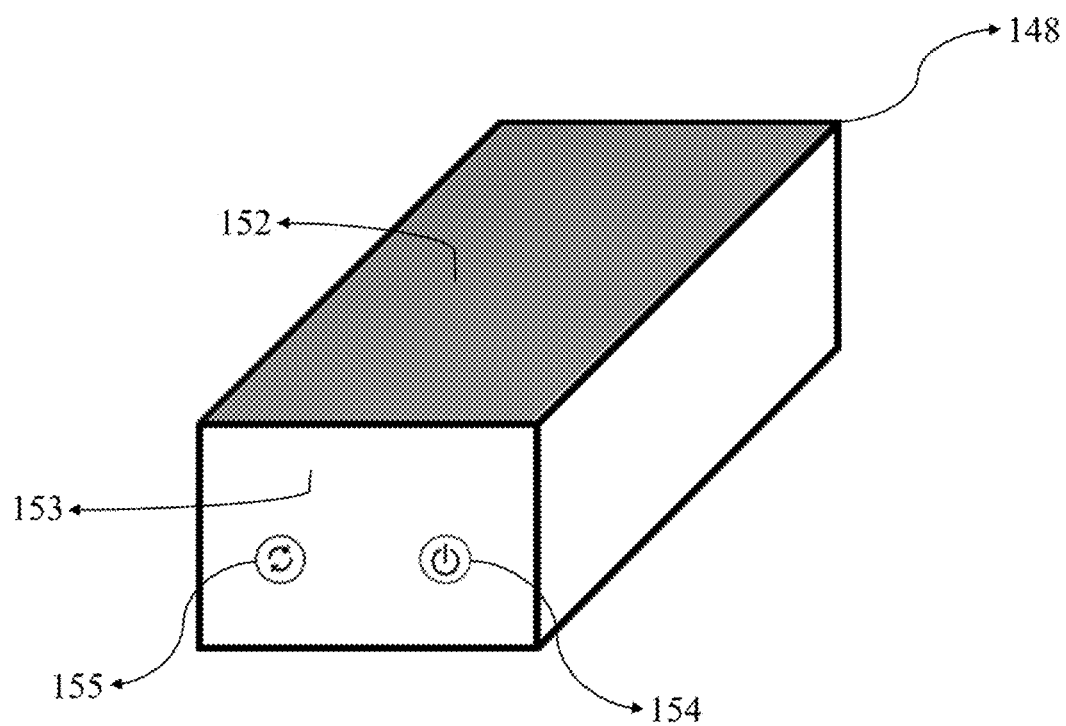
FIG. 13B shows a side isometric of the video camera based accessorial emergency support apparatus.

FIG. 13B is the side isometric view of the accessorial emergency support apparatus. The device 148 has synchronization button 155 and power button 154 embedded on the side surface 153 of the accessorial emergency support apparatus 148. The power button 154 is used for powering on and off the device 148, and operating the other functionalities of the device 148. The power button 154 also sends the device to sleep mode and wakes the device from sleep mode. The synchronization button 155 is utilized for synchronizing the device 148 and data with the primary emergency support apparatus, life-support network and other accessorial devices.

Figure 13C:
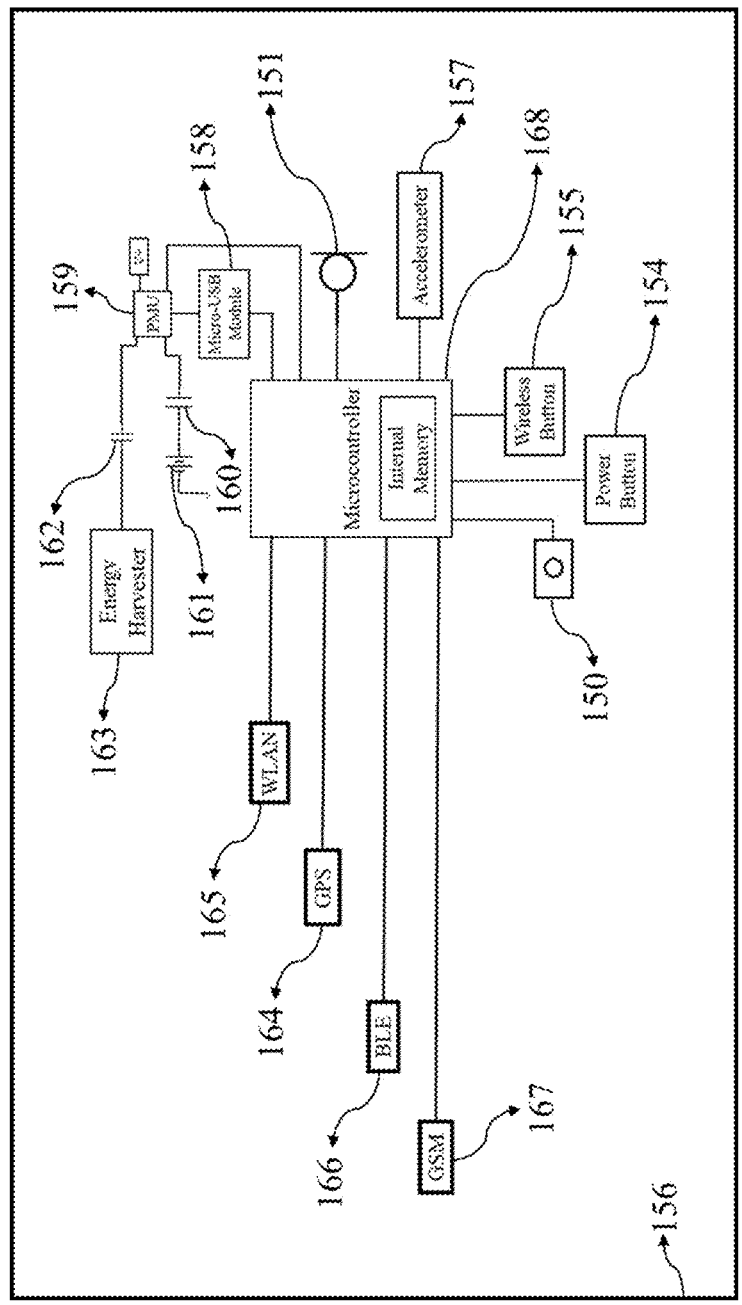
FIG. 13C shows the hardware block diagram of the accessorial emergency support apparatus.

FIG. 13C shows the internal hardware block diagram of the accessorial emergency support apparatus 148. The device 148 has packaged hardware box 156, which comprises of a central microprocessor with internal memory 168, wireless antennae set of 164 166-167, video camera 150, microphone 151, accelerometer 157, power button 154, wireless button 155, power supply unit and other accompanying internal circuitry components. The microprocessor with internal memory 168 of the device 148 is attached to wireless antenna set of WLAN 165, Bluetooth 166, GPS 164 and GSM 167 modules, which are utilized for wirelessly communicating the audio data, video data, location data, movement data and other important information to the life-support network. The GPS 164 and other wireless antennae set 165-166-167 are used to track the speed and location of the device 148. The 9/6-axis accelerometer 157 is utilized as a real-time feedback to cancel motion noise in the recording. The processing as in flow-diagram FIG. 3A or FIG. 3C or both can be applied to remove the movement noise in the recordings through the feedback of the accelerometer. The accelerometer 157 is also used to compute movement related data (like speed, phase, etc). The processing as in flow-diagram as in FIG. 3I to FIG. 3J can be applied to compute movement related data. The hardware 156 has power supply unit comprising of micro-USB module 158, PMU 159, supercapacitor 160-battery 161 set and the supercapacitor 162—energy harvester 163. The USB module 158 is utilized to plug the accessorial emergency support device 148 to external devices, and to power the device 148 and to recharge the internal battery. The PMU 159 manages power supply of the hardware. The supercapacitor 162—energy harvester 163 is used as a renewable method to power the device 148.

Figure 14:
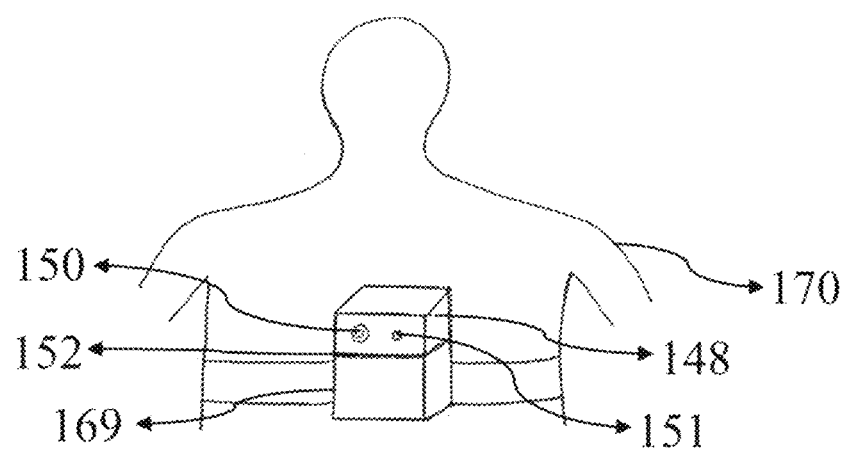
FIG. 14 shows the accessorial video camera device attached to the emergency support apparatus.

FIG. 14 shows the method to attach the accessorial video camera device 148 to a emergency support apparatus. The adhesive component 152 of the accessorial mobile camera device 148 is used for attaching the 148 to the wearable device 169 worn on the user 170. The accessorial emergency support apparatus 148 is affixed on the 169, such that the video camera 150 and mic 151 of the accessorial emergency support apparatus 148 faces the incident perceiving side.

The above described invention disclosure is intended for illustration purposes, and for those skilled in the art may instantly perceive numerous modifications, variations and equivalents. Therefore, the disclosure is not exhaustive in broader aspects and the invention is not limited to specific details, illustrated hardware designs, described computational methods and specific embodiment forms. All equivalents and modifications are intended to be included within the scope of attached claims. Accordingly, additional changes and modifications may be made without departing from the scope or spirit of the invention disclosure appended in the document, claims and their equivalents.

Lexicography

Neural activity as described in the disclosure is obtained from or one or more or combination of the plurality of autonomous neural activity coefficients of $\sigma1$, $\sigma2$, $\sigma3$, $\sigma3/\sigma1$ $\sigma3/\sigma2$, $\sigma2/\sigma1$ and autonomous neural activity assessment parameters of P1, P2, P3, P4 and P5 as disclosed in the current disclosure.

A tracking information, a real-time information, real-time data, tracking data, real-time tracking data and a real-time tracking information are all the same that includes all of the information that can be tracked or extracted or recorded from the or by operation of the emergency support apparatus, the invention, the embodiments or equivalent embodiments. This includes the recorded and the current real-time pressure on the user, the method and the force of the emergency support apparatus (to indicate whether unstrapped by the victimizer or user), the status that whether emergency support apparatus is worn by the user, the mode of transportation, the plurality of movement data and the speed obtained from the accelerometer, the plurality of real-time biological information (accompanied with short description in case of a child tracking or clinical emergency application), the automated medical condition description and predicted clinical conditions (obtained in real-time), the location data, the network data, the proximity of the emergency support apparatus from wireless SWARM devices, the location data recorded from the wireless SWARM devices and a missing note for disclosing more particular information about the user that is recorded by the network of life-support devices, etc.

The invention claimed is:

1. An emergency support apparatus comprising:
  a microprocessor with memory;
  at least one or more biosensor frontend connected to at least one or more biosensors set of an optical biosensors set comprising a green LED, a red LED, an infrared LED, a near infrared LED and a photodetector set, an electrical biosensors set comprising a set of four electrical sensors and a temperature biosensor configured to:
    extract and record a plurality of real-time biological information comprising a heart rate data, an instantaneous heart rate data, a pulse rate variability data, an oxygen saturation data, a neural activity data, a continuous respiratory rate data, an average respiratory rate data, a blood pressure levels data, a blood sugar levels data, a body temperature data, a rapid eye movement sleep cycle data and a non-rapid eye movement sleep cycle data;
    detect and record a plurality of clinical emergency conditions comprising a sleep apnea condition, a hypoglycaemia condition, a hyperglycemia condition, a congestive heart failure condition, a CO poisoning condition, a hypoxia condition, a hypothermia condition, a hyperthermia condition, an anxiety condition and a seizure condition;
an accelerometer configured to:
    remove a plurality of movement errors from a plurality of real-time bio-signals of the biosensors set;
    recognize a speed of the emergency support apparatus;
    detect a mode of transportation and a plurality of movement data of a user comprising a sleeping state, a sitting position, a standing position, a walking state, a running state, a sprinting state, a biking state and a driving state;
a pressure sensor set configured to:
    track a real-time pressure and an abduction range on the user of the emergency support apparatus;
    track a force of removal and a method of removal to indicate whether the emergency support apparatus is aggressively unstrapped by a victimizer;
a wireless antennae set, comprising a Bluetooth, a WLAN, a GSM and a GPS, configured to:
    wirelessly form a SWARM network to communicate with a network of life-support devices operated by a parent, a guardian, a SOS network and a social network through a plurality of wireless SWARM devices;
    track a location and the plurality of movement data;
    wirelessly communicate the plurality of real-time biological information, the plurality of clinical emergency conditions, the speed obtained from the accelerometer, the mode of transportation and the plurality of movement data obtained from the accelerometer, the real-time pressure, the force of removal and the method of removal, the plurality of movement data tracked from the wireless antennae set and the location to a central server, the network of life-support devices and an accessorial mobile device operated by the user;
a display to operate the emergency support apparatus; and
a battery and a power management unit configured to manage and supply power.

2. The emergency support apparatus in claim 1 further comprises a supercapacitor and a battery set attached to the power management unit to supply power to the emergency support apparatus.

3. The emergency support apparatus in claim 1 further comprises an energy harvester module and a supercapacitor set attached to the power management unit to supply renewable power to the emergency support apparatus.

4. The emergency support apparatus in claim 1 further comprises a video camera module and a mic module to record and perceive emergency events.

5. The emergency support apparatus in claim 1, wherein upon triggering of an emergency trigger command by the network of life-support devices or the emergency support apparatus, the emergency support apparatus:
    validates a status of and activates the wireless antennae set of the emergency support apparatus;
    analyzes the pressure sensor set to obtain a recorded and the real-time pressure on the user of the emergency support apparatus or on the emergency support apparatus;
    analyzes the pressure sensor set to obtain the force of removal and the method of removal indicating whether the emergency support apparatus is aggressively unstrapped by the victimizer;
    verifies and obtains a status, whether the emergency support apparatus is worn by the user, by analyzing whether the plurality of real-time biological information is in a realistic range and has a correlation to the user;
    records a location data and a network data from the plurality of wireless SWARM devices of the SWARM network;
    records a proximity data of the emergency support apparatus from the plurality of wireless SWARM devices;
    records the network data from a plurality of wireless connections formed by the wireless antennae set that includes the SWARM network;
    computes a shortest and robust wireless communication pathway from the plurality of wireless connections formed by the wireless antennae set that includes the SWARM network;
    communicates a plurality of tracking information to the network of life-support devices through the plurality of wireless connections that includes the shortest and robust wireless communication pathway, wherein the plurality of tracking information comprises:
        the recorded and the real-time pressure on the user, the force of removal and the method of removal of the emergency support apparatus, the status that whether the emergency support apparatus is worn by the user, the mode of transportation and the plurality of movement data obtained from the accelerometer, the speed obtained from the accelerometer, the plurality of real-time biological information, the location, the network data, the proximity data, the location data recorded from the plurality of wireless SWARM devices and a missing note that is recorded by the network of life-support devices for disclosing more particular information about the user; and
    communicates the plurality of tracking information to a plurality of devices in a location near the emergency support apparatus including the plurality of wireless SWARM devices in the location near the emergency support apparatus, through the plurality of wireless connections and the SWARM network, on trigger of an alert command by the network of life-support devices.

6. The emergency support apparatus in claim 1, wherein the emergency support apparatus:
    recognizes the user at a risk by:
        analysing the pressure sensor set for the abduction range;
        analysing the pressure sensor set for the force of removal and the method of removal indicating that the emergency support apparatus is aggressively unstrapped by the victimizer;
        analysing the biosensors set to validate whether the plurality of real-time biological information is in a realistic range and whether the biosensors set is detecting one or more of the plurality of clinical emergency conditions; and automatically alerts the network of life-support devices on identification of the user at the risk through a plurality of wireless connections formed by the wireless antennae set that includes the SWARM network.

7. The emergency support apparatus in claim 1 further comprises a child tracking application synchronized to the emergency support apparatus, the central server and the network of life-support devices, wherein the child tracking application operated by the network of life-support devices is configured to display:

a user information comprising an age and a gender;

a device status to indicate whether the emergency support apparatus is worn by the user;

the plurality of real-time biological information, the plurality of clinical emergency conditions and the location;

the speed and the mode of transportation obtained from the accelerometer;

the force and the method of removal of the emergency support apparatus indicating whether the emergency support apparatus is aggressively unstrapped by the victimizer;

a vitals monitor to monitor a plurality of detailed live bio-signals of the plurality of real-time biological information;

a missing note having more particular description about the user that is recorded by the network of life-support devices;

an emergency command button, when triggered displays a plurality of tracking information on the network of life-support devices, wherein the plurality of tracking information comprises:

the plurality of real-time biological information, the plurality of clinical emergency conditions, the speed and the mode of transportation obtained from the accelerometer, the location, the force and the method of removal of the emergency support apparatus, the vitals monitor, the device status, the user information and the missing note;

an alert command button, when triggered sends the plurality of tracking information to a plurality of devices in a location near the emergency support apparatus that includes the plurality of wireless SWARM devices in the location near the emergency support apparatus;

a send tracking update that updates and shares the location of the emergency support apparatus to the network of life-support devices; and an abduction alert when the alert command button or the emergency command button is triggered.

8. The emergency support apparatus in claim 1 further comprises a clinical emergency application synchronized to the emergency support apparatus, the central server and the network of life-support devices, wherein the clinical emergency application operated by the network of life-support devices is configured to display:

a user information comprising a user name, an age, a gender, a medical plan and a medical insurance number;

the plurality of real-time biological information, which also includes a short description on the real-time biological information indicating whether the plurality of real-time biological information is normal or abnormal;

the speed and the mode of transportation obtained from the accelerometer and the location;

a vitals monitor to monitor a plurality of detailed live bio-signals of the plurality of real-time biological information;

an automated medical condition description that more particularly describes a present medical condition of the user indicating whether the pattern of the plurality real-time biological information is normal or abnormal;

a predicted clinical condition that indicates the plurality of clinical emergency conditions;

an alert SOS trigger button, when triggered displays a plurality of tracking information on the network of life-support devices operated by the SOS network, wherein the plurality of tracking information comprises:

the user information, the plurality of real-time biological information, the vitals monitor, the speed and the mode of transportation obtained from the accelerometer, the location, the automated medical condition description and the predicted clinical condition;

an alert network trigger button, when triggered displays the plurality of tracking information on the network of life-support devices operated by the parent, the guardian and the social network;

an alert all trigger button, when triggered displays the plurality of tracking information on the network of life-support devices and a plurality of devices in a location near the emergency support apparatus that includes the plurality of wireless SWARM devices in the location near the emergency support apparatus;

a send tracking update that updates and shares the location of the emergency support apparatus to the network of life-support devices; and a medical emergency alert when the alert SOS trigger button, the alert network trigger button or the alert all trigger button is triggered.

9. The emergency support apparatus in claim 1, wherein the emergency support apparatus is embodied in a wearable form, further comprises:

a belt buckle built in with the pressure sensor set to track the real-time pressure, the abduction range, the force of removal and the method of removal indicating whether the emergency support apparatus is aggressively unstrapped by the victimizer;

a magnetically attractable upper buckle element and a magnetic lower buckle element, of the belt buckle, configured to create a magnetic action to magnetically attract to each other, wherein at least a pressure sensor of the pressure sensor set is embedded on an inner side of the magnetically attractable upper buckle element to track the real-time pressure, the abduction range, the force and the method of removal indicating whether the emergency support apparatus is aggressively unstrapped by the victimizer;

a hinge configured to hold the magnetically attractable upper buckle element and the magnetic lower buckle element;

a detachable case, with a belt hole, configured to hold the biosensors set on a contact surface of the user, wherein a foam base configured to avoid a motion error is placed on the contact surface of the detachable case;

a belt, configured to hold the belt buckle and the detachable case, comprising:

an inner foam base configured to avoid a motion error; and a stickable surface pad on a tail end and an adhesive surface pad on an another tail end of the belt configured to firmly hold and fasten the emergency support apparatus on the user.

10. The emergency support apparatus in claim 9, wherein:
the detachable case comprises a sponge base on the contact surface that is configured to avoid the motion error; and
the belt comprises an inner sponge base that is configured to avoid the motion error.

11. The emergency support apparatus in claim 9, wherein the hinge is a spring hinge.

12. The emergency support apparatus in claim 1, wherein the emergency support apparatus is embodied in a wearable form, further comprises:
a frame configured to hold a pressure sensor of the pressure sensor set and the biosensors set on a contact surface of the user, wherein the frame is attached to a strap;
at least an additional pressure sensor, of the pressure sensor set, affixed on a buckle element of the strap, wherein the pressure sensor set is configured to track the real-time pressure, the abduction range, the force of removal and the method of removal indicating whether the emergency support apparatus is aggressively unstrapped by the victimizer; and
a plurality of rounded corners or rounded casing structure, at the contact surface, configured to evade cuts and injuries during events of aggressively unstrapping the emergency support apparatus.

13. The emergency support apparatus in claim 12, wherein the emergency support apparatus further comprises:
at least four pressure sensors of the pressure sensor set, placed at four corners of the frame, configured to track a direction of removal, the real-time pressure, the abduction range, the method of removal and the force of removal indicating whether the emergency support apparatus is aggressively unstrapped by the victimizer; and
a movable magnetic clasp on an another strap of the emergency support apparatus, wherein the buckle element on the strap is configured to be magnetically attracted to the movable magnetic clasp to fasten the emergency support apparatus on the user.

14. The emergency support apparatus in claim 1, wherein the accessorial mobile device operated by the user is synchronized to the emergency support apparatus and comprises:
a touch display configured to operate the emergency support apparatus;
a video camera and a mic configured to:
record and perceive emergency events; and
operate the emergency support apparatus.

15. The emergency support apparatus in claim 1, wherein the central server, the emergency support apparatus and the network of life-support devices is are wirelessly synchronized to an accessorial emergency support apparatus, wherein the accessorial emergency support apparatus comprises:
a hardware box comprising, a microprocessor with internal memory, and:
a video camera and a microphone configured to:
secretively capture a plurality of recordings;
operate the accessorial emergency support apparatus;
an accelerometer configured to:
record a speed and a plurality of movement data comprising a walking data, a running data, a sprinting data, a biking data and a driving data;
act as a real-time feedback for cancelling motion noise in the plurality of recordings;
a wireless antennae set, comprising a WLAN module, a Bluetooth module, a GPS module and a GSM module, configured to:
track a location of the accessorial emergency support apparatus;
communicate the plurality of recordings, the location obtained from the wireless antennae set of the accessorial emergency support apparatus, and the speed and the plurality of movement data obtained from the accelerometer of the accessorial emergency support apparatus to the network of life-support devices;
a battery and a supercapacitor set attached to a power management unit configured to supply and manage power to the accessorial emergency support apparatus;
an energy harvester and a supercapacitor set configured to supply renewable power to the accessorial emergency support apparatus;
a synchronization button on the hardware box, wherein the synchronization button is configured to wirelessly synchronize the accessorial emergency support apparatus to the emergency support apparatus and the network of life-support devices;
a power button on the hardware box, wherein the power button is configured to:
power on and off the accessorial emergency support apparatus;
send the accessorial emergency support apparatus to a sleep mode and a wake mode; and
a detachable adhesive component, on at least a side of the hardware box, configured to attach and mount the accessorial emergency support apparatus to a surface.

16. A wearable emergency support apparatus, comprising a microprocessor with internal memory and synchronized to a central server, comprising:
a belt buckle comprising:
an in-built pressure sensor set configured to:
track a real-time pressure and an abduction range;
track a force of removal and a method of removal to indicate whether the wearable emergency support apparatus is aggressively unstrapped by a victimizer;
automatically recognize a user at a risk by analyzing for the abduction range and the force of removal and the method of removal indicating that the wearable emergency support apparatus is aggressively unstrapped by the victimizer;
a magnetically attractable upper buckle element and a magnetic lower buckle element, of the belt buckle, configured to create a magnetic action to attract to each other, wherein the upper magnetically attractable buckle element comprises:
at least a pressure sensor, of the pressure sensor set, embedded on an inner side configured to track the real-time pressure, the force of removal and the method of removal indicating whether the wearable emergency support apparatus is aggressively unstrapped by the victimizer;
a hinge configured to hold the magnetically attractable upper buckle element and the magnetic lower buckle element;

a detachable case with a belt hole comprising:
  a biosensors set, comprising a temperature biosensor, a blood glucose sensor, a blood pressure sensor, a pulse sensor and a stress sensor, placed on a contact surface of the user, wherein the biosensors set is configured to:
    automatically recognize whether the wearable emergency support apparatus is worn by the user by analysing whether a plurality of real-time bio-signals obtained from the biosensors set is in a realistic range;
  extract a plurality of real-time biological information and identify a plurality of clinical emergency conditions;
  automatically recognize the user at the risk by analysing whether at least one or more of the plurality of clinical emergency conditions are identified;
  an accelerometer configured to:
    remove a motion error from the plurality of real-time bio-signals recorded from the biosensors set;
    recognize a speed of the wearable emergency support apparatus;
    detect a mode of transportation and a plurality of movement data comprising a sleeping state, a sitting position, a standing position, a walking state, a running state, a sprinting state, a biking state and a driving state;
  a wireless antenna set, comprising a Bluetooth, a WLAN, a GSM and a GPS, configured to:
    wirelessly form a SWARM network to communicate with a network of life-support devices operated by a parent, a guardian, a SOS network and a social network through a plurality of wireless SWARM devices;
    record a plurality of location data from the plurality of wireless SWARM devices;
    record a proximity data of the wearable emergency support apparatus from the plurality of wireless SWARM devices;
    record a network data from a plurality of wireless connections formed by the wireless antenna set that includes the network data obtained from the plurality of wireless SWARM devices;
    wirelessly communicate a plurality of tracking information to the central server, the network of life-support devices and an accessorial mobile device operated by the user, wherein the plurality of tracking information comprises:
      the plurality of real-time bio-signals, the plurality of real-time biological information, the plurality of clinical emergency conditions, the speed, the mode of transportation and the plurality of movement data obtained from the accelerometer, the real-time pressure, the force of removal and the method of removal indicating whether the wearable emergency support apparatus is aggressively unstrapped by the victimizer, a status indicating whether the wearable emergency support apparatus is worn by the user, the network data and the plurality of location data;
    automatically communicate the plurality of tracking information to the network of life-support devices, when the user at the risk is recognized automatically or an emergency command button is triggered through a child tracking application operated by the network of life-support devices;
    communicate the plurality of tracking information to a plurality of devices in a location near the wearable emergency support apparatus that includes the plurality of wireless SWARM devices in the location near the wearable emergency support apparatus, when an alert command button is triggered through a child tracking application operated by the network of life-support devices;
  a battery and a power management unit configured to manage and supply power;
  an energy harvester and a supercapacitor configured to supply renewable power;
  a foam base or a sponge base on the contact surface of the detachable case, wherein the foam base or the sponge base is configured to avoid the motion error;
  a belt configured to hold the belt buckle and the detachable case, wherein the belt comprises:
    an inner foam base or an inner sponge base configured to avoid the motion error; and
    a stickable surface pad on a tail end and an adhesive surface pad on an another tail end of the belt configured to fasten and firmly hold the wearable emergency support apparatus on the user.

17. A wearable emergency support apparatus comprising a microprocessor with internal memory and synchronized to a central server, comprising:
  a frame comprising:
    at least four pressure sensors placed on a contact user of a user, wherein the four pressure sensors, placed at four corners of the frame, are configured to:
    track a real-time pressure;
    track a direction of removal, a force of removal and a method of removal to indicate whether the wearable emergency support apparatus is aggressively unstrapped by a victimizer;
    automatically recognize the user at a risk by analyzing for an abduction range and the force of removal and the method of removal indicating that the wearable emergency support apparatus is aggressively unstrapped by the victimizer;
  a biosensors set, comprising a temperature biosensor, a blood glucose sensor, a blood pressure sensor, a pulse sensor and a stress sensor, placed on the contact surface of the user, wherein the biosensors set is configured to:
    automatically recognize whether the wearable emergency support apparatus is worn by the user by analysing whether a plurality of real-time bio-signals obtained from the biosensors set is in a realistic range;
    extract a plurality of real-time biological information and identify a plurality of clinical emergency conditions;
    automatically recognize the user at the risk by analysing whether at least one or more of the plurality of clinical emergency conditions are identified;
  an accelerometer configured to:
    remove a motion error from the plurality of real-time bio-signals recorded from the biosensors set;
    recognize a speed of the wearable emergency support apparatus;
    detect a mode of transportation and a plurality of movement data comprising a sleeping state, a sitting position, a standing position, a walking state, a running state, a sprinting state, a biking state and a driving state;
  a wireless antenna set, comprising a Bluetooth, a WLAN, a GSM and a GPS, configured to:
    wirelessly form a SWARM network to communicate with a network of life- support devices operated by a parent, a guardian, a SOS network and a social network through a plurality of wireless SWARM devices;

record a plurality of location data from the plurality of wireless SWARM devices;

record a proximity data of the wearable emergency support apparatus from the plurality of wireless SWARM devices;

record a network data from a plurality of wireless connections formed by the wireless antenna set that includes the network data obtained from the plurality of wireless SWARM devices;

wirelessly communicate a plurality of tracking information to the central server, the network of life-support devices and an accessorial mobile device operated by the user, wherein the plurality of tracking information comprises:

the plurality of real-time bio-signals, the plurality of real-time biological information, the plurality of clinical emergency conditions, the speed, the mode of transportation and the plurality of movement data obtained from the accelerometer, the real-time pressure, the direction of removal, the force of removal and the method of removal indicating whether the wearable emergency support apparatus is aggressively unstrapped by the victimizer, a status indicating whether the wearable emergency support apparatus is worn by the user, the network data and the plurality of location data;

automatically communicates the plurality of tracking information to the network of life-support devices, when the user at the risk is recognized automatically or an emergency command button is triggered through a child tracking application operated by the network of life-support devices;

communicates the plurality of tracking information to a plurality of devices in a location near the wearable emergency support apparatus that includes the plurality of wireless SWARM devices in the location near the wearable emergency support apparatus, when an alert command button is triggered through a child tracking application operated by the network of life-support devices;

a battery and a power management unit configured to manage and supply power;

an energy harvester and a supercapacitor configured to supply and manage renewable power;

a buckle element, attached to the frame and a front strap, comprising:

at least an additional pressure sensor, wherein the pressure sensors are configured to track the real-time pressure, the force of removal and the method of removal to indicate whether the wearable emergency support apparatus is aggressively unstrapped by the victimizer;

a plurality of rounded edges at the corners of the contact surface or a rounded casing structure at the contact surface, wherein they are configured to evade cuts and injuries during events of aggressively unstrapping the wearable emergency support apparatus; and a buckle tongue on the buckle element, wherein the buckle tongue goes through a plurality of adjustment holes on a back strap to fasten the wearable emergency support apparatus on the user.

* * * * *